(12) United States Patent
Gruber et al.

(10) Patent No.: US 9,320,738 B2
(45) Date of Patent: Apr. 26, 2016

(54) FORMULATIONS OF 5-FLUOROCYTOSINE AND USES THEREOF

(75) Inventors: Harry E. Gruber, Rancho Santa Fe, CA (US); Douglas J. Jolly, Encinitas, CA (US); Kay Olmstead, San Diego, CA (US)

(73) Assignee: Tocagen Inc., San Diego, CA (US)

( * ) Notice: Subject to any disclaimer, the term of this patent is extended or adjusted under 35 U.S.C. 154(b) by 259 days.

(21) Appl. No.: 13/001,516

(22) PCT Filed: Jun. 30, 2009

(86) PCT No.: PCT/US2009/049322
§ 371 (c)(1),
(2), (4) Date: Mar. 11, 2011

(87) PCT Pub. No.: WO2010/002937
PCT Pub. Date: Jan. 7, 2010

(65) Prior Publication Data
US 2011/0268720 A1 Nov. 3, 2011

Related U.S. Application Data

(60) Provisional application No. 61/077,142, filed on Jun. 30, 2008.

(51) Int. Cl.
*A61K 9/20* (2006.01)
*A61K 31/513* (2006.01)
(Continued)

(52) U.S. Cl.
CPC ............. *A61K 31/513* (2013.01); *A61K 9/2009* (2013.01); *A61K 9/2018* (2013.01); *A61K9/2027* (2013.01); *A61K 9/2054* (2013.01); *A61K 31/4196* (2013.01); *A61K 31/496* (2013.01); *A61K 31/505* (2013.01); *A61K 31/7048* (2013.01); *A61K 38/51* (2013.01)

(58) Field of Classification Search
USPC .......................................... 424/464
See application file for complete search history.

(56) References Cited

U.S. PATENT DOCUMENTS 6,667,060 B1 * 12/2003 Vandecruys et al. .......... 424/488
6,677,155 B1    1/2004 Sena-Esteves et al.
(Continued)

FOREIGN PATENT DOCUMENTS

JP    2002-512946    5/2002
JP    2004-501190    1/2004
(Continued)

OTHER PUBLICATIONS

Lacy et al. (Drug Information Handbook, 7th Edition, 1999-2000, pp. 489-490, Flucytosine.*
(Continued)

*Primary Examiner* — San-Ming Hui
(74) *Attorney, Agent, or Firm* — Joseph R. Baker, Jr.; Gavrilovich, Dodd & Lindsey LLP

(57) ABSTRACT

The disclosure provides an extended release formulation of 5-fluorocytosine. In another aspect, a method of treating a fungal disease is provided. The method comprises administering to a subject in need thereof a fungus-treating effective amount of a composition comprising 5-fluorocytosine. In yet another aspect, a method of treating a cancer is provided. The method comprises administering to a subject in need thereof a sufficient amount of an expression vector to induce expression of cytosine deaminase which is capable of converting 5-fluorocytosine to 5-fluorouracil in cells of the cancer and a cancer-treating effective amount of a composition comprising 5-fluorocytosine.

68 Claims, 4 Drawing Sheets

(51) Int. Cl.
  A61K 31/4196  (2006.01)
  A61K 31/496   (2006.01)
  A61K 31/505   (2006.01)
  A61K 31/7048  (2006.01)
  A61K 38/51    (2006.01)

(56) References Cited

U.S. PATENT DOCUMENTS

| | | | |
|---|---|---|---|
| 7,186,699 B2 | 3/2007 | Harding et al. | |
| 2004/0062805 A1* | 4/2004 | Vandecruys et al. | 424/471 |
| 2005/0031593 A1 | 2/2005 | Harding et al. | |
| 2005/0049207 A1 | 3/2005 | Kaufmann | |
| 2005/0186179 A1 | 8/2005 | Harats et al. | |
| 2006/0003005 A1 | 1/2006 | Cao et al. | |
| 2007/0190140 A1 | 8/2007 | Alaux et al. | |
| 2009/0068287 A1 | 3/2009 | Welsh et al. | |
| 2009/0170876 A1 | 7/2009 | Qasem et al. | |
| 2012/0052554 A1 | 3/2012 | Kasahara et al. | |

FOREIGN PATENT DOCUMENTS

| | | |
|---|---|---|
| JP | 2008-509973 | 4/2008 |
| WO | 92/15308 A1 | 9/1992 |
| WO | 99/55305 | 11/1999 |
| WO | 0104266 A1 | 1/2001 |
| WO | 02/00213 A1 | 1/2002 |
| WO | 2006127980 A2 | 11/2006 |
| WO | 2007/069358 A1 | 6/2007 |
| WO | 2010036986 | 4/2010 |
| WO | 2010045002 A3 | 4/2010 |
| WO | 2011126864 A2 | 10/2011 |
| WO | 2012021794 A1 | 2/2012 |

OTHER PUBLICATIONS

Bonny et al. (Use of In Vitro Release Tests for the Prediction of the In Vivo Behavior and the Development of Flucytosine Controlled-Release Capsule, Journal of Pharmaceutical Sciences, vol. 84, No. 5, May 1995, pp. 619-623.*
Baumgartner et al., International Journal of Pharmaceutics, 2000;195:125-135.*
Young, Lee W., International Search Report and Written Opinion, PCT/US2009/049322, United States Patent & Trademark Office, Sep. 2, 2009.
Vermes et al., "Flucytosine: a review of its pharmacology, clinical indictions, pharmacokinetics, toxicity and drug interactions." J. of Antimicrobial Chemotherapy, 2000, pp. 171-179, vol. 46.
Nisihiyama, "Antineoplastic effects in rats of 5-fluorocytosine in combination with cytosine deaminase capsules," Cancer Res. 45:1753-1761 (1985).
Pai et al., "Clinical pharmacokinetics of oral controlled-release 5-fluorocystosine," Antimicrob. Agents Chemother. 54 (3):1237-41 (2010); epub Dec. 28, 2009.
Paola et al., "Suicide Gene Therapy With the Yeast Fusion Gene Cytosine Deaminase/Uracil Phosphoribosyltransferase is Not Enough For Pancreatic Cancer," Pancreas 35(3):224-231 (2007).
Smith et al., "Therapeutic drug monitoring of antifungals: pharmacokinetic and pharmacodynamic considerations," Ther. Drug. Monit. 30(2):167-72 (2008).
Sotos et al., "Preclinical and clinical aspects of biomodulation of 5-fluorouracil," Cancer Treat. Rev. 20:11-49 (1994).
Tai et al., "Single-Shot, Multicycle Suicide Gene Therapy by Replication-Competent Retrovirus Vectors Achieves Long-Term Survival Benefit in Experimental Glioma," Molecular Therapy 12(5):842-851 (2005).
Vakil et al., "Combination of antifungal therapy involving amphotericin B, rapamycin and 5-fluorocytosine using PEG-phospholipid micelles," Pharm. Res. 25(9):2056-64 (2008); Epub Apr. 28, 2008.
Vandenbussche, H. L. et al., "Stability of flucytosine 50 mg/ml in extemporaneous oral liquid formulations," Am. J. Health Syst. Pharm. 59(19):1853-5 (2002).
Vermes, A. et al., "An accelerated stability study of 5-flucytosine in intravenous solution," Pharm. World Sci. 21 (1):35-9 (1999).
Vermes et al., "Flucytosine: correlation between toxicity and pharmacokinetic parameters," Chemotherapy 46:86 (2000).
Vermes et al., "Prediction of flucytosine-induced thrombocytopenia using creatinine clearance," Chemotherapy 46:335 (2000).
Vermes et al., "An in vitro study on the active conversion of flucytosine to fluorouracil by microorganisms in the human intestinal microflora," Chemotherapy 49:17-23 (2003).
Wallace et al., "Intratumoral Generation of 5-Fluorouracil Mediated by an Antibody-Cytosine Deaminase Conjugate in Combination with 5-Fluorocytosine," Cancer Res. 54:2719 (1994).
Wang et al., "Highly Efficient and Tumor-Restricted Gene Transfer to Malignant Gliomas by Replication-Competent Retroviral Vectors," Human Gene Therapy 14:117-127 (2003).
Wang et al., "Use of replication-competent retroviral vectors in an immunocompetent intracranial glioma model," Neurosurg. Focus 20(4):E25 (2006).
Warmann et al., "Adenovirus-mediated cytosine deaminase/5-fluorocytosine suicide gene therapy of human hepatoblastoma in vitro," Pediatric Blood & Cancer, 53: 145-151 (2009).
Wintermeyer, S. M. et al., "Stability of flucytosine in an extemporaneously compounded oral liquid," Am. J. Health Syst. Pharm. 53(4):407-9 (1996).
Yao et al., "Product release is rate-limiting in the activation of the prodrug 5-fluorocytosine by yeast cytosine deaminase," Biochemistry 44(15):5940-7 (2005).
Young, Lee W. International Search Report and Written Opinion. International Application No. PCT/US2009/049322. Date of mailing: Sep. 2, 2009.
Zhang et al., "A novel oncolytic adenovirus expressing *Escherichia coli* cytosine deaminase exhibits potent antitumor effect on human solid tumors," Cancer Biother. Radiopharm 25(4):487-95 (2010).
Heo, Joo Hyung, International Search Report and Written Opinion, PCT/US2013/066709, Korean Intellectual Property Office, Date of Mailing: Jan. 28, 2014.
Schifferer, Hermann, Extended European Search Report, European Patent Application No. 09774387.6, Aug. 27, 2012.
Yoshida, Kayoko, Office Action, Japanese Patent Application No. 2011-516833, Oct. 15, 2013.
Valencia Hernandez, Armando, Patent Application No. MX/a/2010/014256, Mexican Patent Office, Jul. 2013.
Goolam, Safiea, Office Action, Australian Patent Application No. 2013205004, Date of Issue: Mar. 13, 2015.
Valencia Hernandez, Armando, Patent Application No. MX/a/2010/014256, Mexican Patent Office, May 19, 2015.
Aghi et al., "Synergistic Anticancer Effects of Ganciclovir/Thymidine Kinase and 5-Fluorocytosine/Cytosine Deaminase Gene Therapies," J. Natl. Cancer Inst. 90(5):370-380 (1998).
Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).
Akbulut et al., "Vector targeting makes 5-fluorouracil chemotherapy less toxic and more effective in animal models of epithelial neoplasms," 10(22):7738-46 (2004).
Akimoto, et al., "A new delivery system for 5-fluorouracil using prodrug and converting enzyme," Br. J. Ophthalmol 86:581-586 (2002).
Allen et al., "Stability of acetazolamide, allopurinol, azathioprine, clonazepam, and flucytosine in extemporaneously compound oral liquids," Am J. Health Syst. Pharm. 53(16):1944-9 (1996).
Ancobon (flucytosine)250-500mg Capsule, Valeant Pharmaceuticals, Inc. Package insert. at http://www.valeant.com/fileRepository/products/PI/Ancobon_Capsule%20250-500mg_PI_Sep01.pdf.
Andes et al., "In vivo characterization of the pharmacodynamics of flucytosine in a neutropenic murine disseminated candidiasis model.," Antimicrob. Agents Chemother. 44:938-942 (2000).

(56) References Cited

OTHER PUBLICATIONS

Andes et al., "Antifungal therapeutic drug monitoring: established and emerging indications," Antimicrob. Agents Chemother. 53:24 (2009).
Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (200).
Beijer, Gijsbertus. International Preliminary Report on Patentability. International Application No. PCT/US2009/058510. Date of mailing: Apr. 7, 2011.
Beijer, Gijsbertus. International Preliminary Report on Patentability. International Application No. PCT/US2009/058512. Date of Mailing: Apr. 7, 2011.
Bellman R. "Clinical pharmacokinetics of systemically administered antimycotics," Curr. Clin. Pharmacol. 2(1):37-58 (2007).
Bennet, J. E., "Flucytosine," Ann. Intern. Med. 86(3):319-21 (1977).
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Block et al., "Pharmacological Studies with 5-Fluorocytosine," Antimicrobial Agents and Chemotherapy 1(6):476-482 (1972).
Bonny, J. D. et al., "Use of in vitro release tests for prediction of the in vivo behavior and the development of flucytosine controlled-release capsules," J. Pharm. Sci. 84(5):619-23 (1995).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).
Brouwer, A. E. et al., "Oral versus intravenous flucytosine in patients with human immunodeficiency virus-associated cryptococcal meningitis," Antimicrob. Agents Chemother. 51(3):1038-42 (2007); Epub Dec. 2, 2006.
Chaszczewska-Markowska et al., "Liposomal formulation of 5-fluorocystosine in suicide gene therapy with cytosine deaminase—for colorectal cancer," Cancer Letters 262:164-172 (2008).
Chio, Jun Ho. International Search Report and Written Opinion. International Application No. PCT/US2009/058510. Date of mailing of the International Search Report Jul. 6, 2010.
Cho, Jeong Han. International Search Report and Written Opinion. International Application No. PCT/US2009/058512. Date of mailing of the Report: May 11, 2010.
Daneshmend et al., "Clinical pharmokinetics of systemic antifugal drugs," Clin. Pharmacokinet. 8:17 (1983).
Dias et al. "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Erbs et al., "In Vivo Cancer Gene Therapy by Adenovirus-mediated Transfer of a Bifunctional Yeast Cystosine Deaminase/Uracil Phosphoribosyltransferase Fusion Gene," Cancer Research 60(14):3813-3822 (2000).
Erbs et al. "Modified vaccinia virus Ankara as a vector for suicide gene therapy," Cancer Gene Ther. 15(1):18-28 (2008); Epub Nov. 9, 2007.
Fischer et al., "Mechanisms of thymidine kinase/ganciclovir and cytosine deaminase/5-fluorocytosine suicide gene therapy-induced cell death in glioma cells," Oncogene 24:1231-1243 (2005).
Foloppe et al., "Targeted delivery of a suicide gene to human colorectal tumors by a conditionally replicating vaccinia virus," Gene Ther. 15(20):1361-71 (2008); Epub May 15, 2008.
Freytag et al., "Phase I Study of Replication-competent Adenovirus-mediated Double Suicide Gene Therapy for the Treatment of Locally Recurrent Prostate Cancer," Cancer Res. 62:4968 (2002).
Giffo-Schmitt, Beate. International Preliminary Report on Patentability. International Application No. PCT/US2009/049322. Date of Issuance of Report: Jan. 5, 2011.
Goodwin, M. L. et al., "Antifungal serum concentration monitoring: an update," J. Antimicrob. Chemother. 61 (1):17-25 (2008); Epub Nov. 12, 2007.

Groll et al., "Clinical pharmacology of antifungal compounds," Infect. Dis. Clin. North Am. 17(1):159-91, ix (2003).
Guffey et al., "Engineered herpes simplex virus expressing bacterial cytosine deaminase for experimental therapy for brain tumors," 14(1):45-56 (2006); Epub Sep. 22, 2006.
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).
Hiraoka et al., "Therapeutic Efficacy of Replication-Competent Retrovirus Vector-Mediated Suicide Gene Therapy in a Multifocal Colorectal Cancer Metastasis Model," Cancer Research 67(11):5345-5353 (2007).
Hirschowitz et al., "In vivo adenovirus-mediated gene transfer of the *Escherichia coli* cytosine deaminase gene to human colon carcinoma-derived tumors induces chemosensitivity to 5-fluorocytosine," Hum. Gene Ther. 6(8):1055-63 (1995).
Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase," PNAS 91(17):8302-8306 (1994).
Kauffman et al., "Bone marrow toxicity associated with 5-fluorocytosine therapy," Antimicrob. Agents Chemother. 11 (2):244-7 (1977).
Kawasaki et al., "Replication-competent retrovirus vector-mediated prodrug activator gene therapy in experimental models of human malignant mesothelioma," Cancer Gene Therapy 18:571-578 (2011).
Kikuchi et al., "Highly Efficient Gene Delivery for Bladder Cancers by Intravesically Administered Replication-Competent Retroviral Vectors," Clin. Cancer Res. 13:4511-4518 (2007).
Kurozumi et al., "Apotosis Induction With 5-Fluorocytosine/Cytosine Deaminase gene therapy for Human Malignant Glioma Cells Mediated by Adenovirus," Journal of Neuro-Oncology 66(1-2):117-127 (2004).
Lewis, R. E., "Pharmacodynamic implications for use of antifungal agents," Curr. Opin. Pharmacol. 7(5):491-7 (2007); Epub Jul. 9, 2007.
Liu et al. "Engineering conditionally replication-competent adenoviral vectors carrying the cytosine deaminase gene increase the infectivity and therapeutic effect for breast cancer gene therapy," 13(4):346-56 (2006).
Lu et al., "Highly efficient gene transfer to solid tumors in vivo by tumor-selective replicating retrovirus vectors," Int. J. Mol. Med. 25(5):769-75 (2010).
Lyman et al., "Systemically administered antifungal agents. A review of their clinical pharmacology and therapeutic applications," Drugs 44(1):9-35 (1992).
Maguire, Simon. Examination Report. New Zealand Application No. 592070. Date of Report: May 24, 2011.
Manjunath et al., "Clinical Pharmokinetics of Oral Controlled-Release 5-Fluorocytosine," 54(3):1237-1241 (2010).
Miller et al., "Intratumurol 5-Fluorouracil Produced by Cytosine Deaminase/5-Fluorocytosine Gene Therapy Is Effective for Experimental Human Glioblastomas," Cancer Res. 62:773 (2002).
Mullen et al., "Transfer of the bacterial gene for cytosine deaminase to mammalian cells confers lethal sensitivity to 5-fluorocytosine: a negative selection system," PNAS 89(1):33-37 (1992).
Nakamura et al., "Multimodality Therapy with a Replication-conditional Herpes Simplex Virus 1 Mutant that Expresses Yeast Cytosine Deaminase for intratumoral Conversion of 5-Fluorocytosine to 5-Fluorouracil," Cancer Res. 61:5447-5452 (2001); Epub Jul. 1, 2001.
Negroni et al., "Treatment of colon cancer cells using the cytosine deaminase/5-fluorocytosine suicide system induces apotosis, modulation of the proteome, and Hsp90B phsophorylation," Molecular Cancer Therapeutics 6:2747-2756 (2007).
Armando Valencia Hernandez, Office Action, Mexican Patent Application No. MX/2014/040260, Oct. 7, 2014.

\* cited by examiner

FORMULATIONS OF 5-FLUOROCYTOSINE AND USES THEREOF

CROSS REFERENCE TO RELATED APPLICATIONS

This application is a U.S. National Stage application filed under 35 U.S.C. §371 and claims priority to International Application No. PCT/US09/49322, filed Jun. 30, 2009, which application claims priority under 35 U.S.C. §119 to U.S. Provisional Application No. 61/077,142, filed Jun. 30, 2008, the disclosures of which are incorporated herein by reference.

TECHNICAL FIELD

The invention relates to formulations of 5-fluorocytosine, and to methods of using formulations of 5-fluorocytosine for treating fungal diseases, *pneumocystis carinii* pneumonia and other infectious diseases or cancer.

BACKGROUND

The pyrimidine analog 5-fluorocytosine (5-FC) is a synthetic drug (Ancobon®) which has antimycotic activity and can also be used for treatment of cancer. Ancobon® is an immediate release capsule formulation with a short half life of drug, is rapidly cleared from the body and, thus, high frequent dosing of 4 to 16 times a day is required to maintain the efficacy level of the drug.

Furthermore, 5-FC is effective at or above a minimum trough level of drug concentration in the blood and even with frequent dosing of Ancobon, because of its immediate release nature, there are periods of time when the drug concentration falls below this effective concentration.

5-FC was first synthesized in 1957. It has no intrinsic antifungal capacity, but after it has been taken up by susceptible fungal cells, it is converted into 5-fluorouracil (5-FU), which is further converted to metabolites some of which interfere with fungal RNA and DNA synthesis. Monotherapy with 5-FC is limited because of the frequent development of resistance. In combination with amphotericin B, 5-FC can be used to treat severe systemic mycoses, such as cryptococcosis, candidosis, chromoblastomycosis and aspergillosis. Recently, 5-FC has been combined with newer azole antifungal agents; it also plays an important role in a new approach to the treatment of cancer. The severe side effects of 5-FC include hepatotoxicity and bone-marrow depression. Transient nausea occurs at the time of dosing which can be improved by spreading the dose out over a few minutes during a particular dose. Gastrointestinal symptoms are also observed. In most patients, these side effects are concentration dependent, predictable, possibly avoidable with close monitoring to maintain 5-FC concentrations at <100 µg/ml, and reversible with drug discontinuation or reduction of dose. 5-FC is well absorbed after oral administration, penetrates into body tissues well, including the brain, and is excreted mainly by the kidneys. In renal failure, major dose adjustments have to be made. The most important drug interaction of 5-FC occurs with concomitant administration of 5-FC and nephrotoxic drugs, especially amphotericin B.

SUMMARY

The disclosure provides a sustained/extended (sometimes referred to as a "slow") release formulation of a prodrug useful in fungal, cancer, infectious disease and other disease therapies. The extended release formulation is useful for improving patient compliance with administration by reducing the dosing frequency and by reducing side-effects. The extended release formulation of the disclosure provides an extended $T_{max}$ compared to currently available immediate dose formulations (e.g., Ancobon®).

The disclosure provides an extended release 5-FC formulation. When dosed appropriately, the extended release 5-FC formulation provides peak blood levels of 5-FC between about 1-200 µg/ml (e.g., between about 1-100 µg/ml, about 20-90 µg/ml, about 30-80 µg/ml, about 40-70 µg/ml or about 80-120 µg/ml). It is to be understood that any value between about 1-200 µg/ml is contemplated by the disclosure. In one embodiment, the levels of 5-FC are obtained by administering an extended release dose formulation of about 1 to 5 g per dose 3-4 times per day (e.g., 3 times per day). In one embodiment, the levels of 5-FC are obtained using an extended release dose formulation of the disclosure administered 1-4 times per day (about 50-200 mg/kg/day). In one embodiment, the levels of 5-FC are obtained using an extended release dose formulation of the disclosure administered 1-3 times per day (about 50-200 mg/kg/day). In one embodiment, the levels of 5-FC are obtained using an extended release dose formulation of the disclosure administered 1-2 times per day (about 50-250 mg/kg/day). In one embodiment, the levels of 5-FC are obtained using an extended release dose formulation of the disclosure administered 2-4 times per day (about 50-250 mg/kg/day). In one embodiment, the levels of 5-FC are obtained using an extended release (i.e., an extended release) dose formulation of the disclosure administered 2-3 times per day (about 50-250 mg/kg/day). In one embodiment, the 5-FC formulation of the disclosure is used to treat a subject for 7 days out of every month for months or years. In another embodiment, the dose can be from about 1 to 5 g administered 3-4 doses per day. In yet another embodiment, the 5-FC formulation of the disclosure is administered from about 2 to 8 g (e.g., about 6 to 7 g) 2 or more times per day. In a further embodiment, the dose is administered 1 time per day at 50-200 mg/kg, 2 times per day at 25-100 mg/kg, three times per day at about 16-67 mg/kg, or 4 times per day at 12-50 mg/kg. Again it will be recognized that any dose between 1-250 (e.g., 75-175) mg/kg per day can be included, the dosing schedule adjusted to achieve the desired amount and serum levels or for decreased renal function. In yet another embodiment, the 5-FC formulation provides one or more of the following in a fed human subject following a single dose of 500 mg 5-FC in an extended release formulation: (i) a 5-FC $C_{max}$ of between about 2.0 µg/ml and about 10.0 µg/ml (e.g., between about 2.0-9.5 µg/ml, between about 3.0-8.0 µg/ml, between about 3.0-6.0 µg/ml, between about 3.5-8.0 µg/ml, or between about 2.5-4.5 µg/ml); (ii) a $t_{median}$ of about 3 hrs or greater, (e.g., between about 3-12 hrs, between about 3-10 hrs, between about 4-12 hrs, between about 4-10 hrs, between about 5-12 hrs, between about 5-10 hrs, between about 6-12 hrs, or between about 6-10 hrs, or between about 6-8 hrs); (iii) an AUC of about 20-80 µg*hr/ml (e.g., between about 25-75 µg*hr/ml, between about 30-70 µg*hr/ml, between about 30-65 µg*hr/ml, between about 30-60 µg*hr/ml, or between about 35-65 µg*hr/ml); and (iv) a $t_{1/2}$ of between about 3-8 hrs (e.g., between about 3-7 hrs, between about 4-8 hrs, or between about 4-7 hrs). In one embodiment, the dose of 5-FC is adjusted based upon the activity of cytosine deaminase activity within a subject, tissue or cell. In yet another embodiment, the 5-FC formulation provides one or more of the following in a fed human subject following a single dose of 100 to 1000 mg 5-FC in an extended release formulation: (i) a 5-FC $C_{max}$ of between about 2.0 µg/ml and about 10.0 µg/ml scaled linearly for the multiple of the 500 mg dose; (ii) a $t_{median}$ of about 3 hrs or greater, (e.g., between about 3-12 hrs, between about 3-10 hrs, between about 4-12 hrs, between about 4-10 hrs, between about 5-12 hrs, between about 5-10 hrs, between about 6-12 hrs, or between about 6-10 hrs, or between about 6-8 hrs); (iii) an AUC of about 20-80 µg*hr/ml scaled linearly for the multiple of the 500 mg dose; and (iv) a $t_{1/2}$ of between about 3-8 hrs (e.g., between about 3-7 hrs, between about 4-8 hrs, or between about 4-7 hrs). In one embodiment, the disclosure provides an oral pharmaceutical composition comprising 5-FC, wherein the pharmaceutical composition is a modified release form (e.g., a monolithic solid tablet form) and releases 5-FC into the upper gastrointestinal tract of a subject over a sustained period of time. The composition can further comprise a hydrophilic matrix forming polymer such as one or more of carbopol (e.g., carbopol 71-G), polyvinyl acetate and povidone co-polymer (Kollidon-SR®) hydroxypropyl cellulose (HPC), hydroxymethyl cellulose (HPMC), and polyethylene oxide (PolyOx). The hydrophilic polymers can make up about 10 weight percent to about 40 weight percent (or more) of the composition. In one embodiment, the 5-FC is present in an amount of about 100 mg to about 1000 mg per tablet or dose. In another embodiment, the composition exhibits 5-FC release rate of greater than about 80% within about 4 to about 12 hours (e.g., about 6-10 hours) as measured by the USP Type II dissolution apparatus (paddle method) at 75 rpm in 900 ml deionized water at 37° C. using 5-FC USP method with UV detection at about 275 nm. In yet another embodiment, the 5-FC is present in the pharmaceutical composition in an amount of about 500 mg and wherein after oral administration of the pharmaceutical composition to a fed subject (e.g., a fed human subject), the composition exhibits one or more of: (i) a 5-FC $C_{max}$ of between about 2.0 µg/ml and about 10.0 µg/ml (e.g., between about 2.0-9.5 µg/ml, between about 3.0-8.0 µg/ml, between about 3.0-6.0 µg/ml, between about 3.5-8.0 µg/ml, or between about 2.5-4.5 µg/ml); (ii) a $t_{median}$ of about 3 hrs or greater, (e.g., between about 3-12 hrs, between about 3-10 hrs, between about 4-12 hrs, between about 4-10 hrs, between about 5-12 hrs, between about 5-10 hrs, between about 6-12 hrs, or between about 6-10 hrs, or between about 6-8 hrs); (iii) an AUC of about 20-80 µg*hr/ml (e.g., between about 25-75 µg*hr/ml, between about 30-70 µg*hr/ml, between about 30-65 µg*hr/ml, between about 30-60 µg*hr/ml, or between about 35-65 µg*hr/ml); and (iv) a $t_{1/2}$ of between about 3-8 hrs (e.g., between about 3-7 hrs, between about 4-8 hrs, or between about 4-7 hrs). In yet another embodiment, after 7 days of dosing of oral administration of the 5-FC pharmaceutical composition to a fed subject at about 150 mg/Kg/day dosing schedule, the composition exhibits (i) a mean plasma concentration of 5-FC of between about 20 and 100 µg/ml, about 30 and 80 µg/ml about 20 and 70 µg/ml, about 30 and 80 µg/ml, about 5 and 50 µg/ml, about 5 and 40 µg/ml, about 5 and 30 µg/ml, or about 5 and about 20 µg/ml. In yet another embodiment, after 7 days of dosing of oral administration of the 5-FC pharmaceutical composition to a fed subject at about 175 mg/Kg/day dosing schedule, the composition exhibits a mean plasma concentration of 5-FC of between about 40 and 120 µg/ml, about 50 and 110 µg/ml, about 50 and about 110 µg/ml, or about 60 and about 100 µg/ml. In one embodiment, the total AUC in a fed human is bioequivalent within to the current immediate release formulation of 5-FC or within about 70-120% of the current immediate release formulation.

The disclosure also provides a composition with a formulation comprising 5-FC for extended release. In one embodiment, the formulation comprises about 40-50% w/w 5-fluorocytosine, about 10-20% w/w hydrophilic polymer, about 5-15% w/w binding agent, about 10-30% w/w diluents, and about 0.5-1.5% lubricant. In some embodiments, a core tablet comprising the formulation above may further include a coating of about 1-3% w/w. Formulations as set forth above exhibit a 5-FC release rate by in vitro dissolution of greater than about 80% within about 4 to about 12 hours as measured by the USP Type II dissolution apparatus (paddle method) at 75 rpm in 900 ml deionized water at 37° C. using 5-FC USP method with UV detection at about 275 nm. In another embodiment, the formulation exhibits, after a single dose oral administration to a fed subject (e.g., a fed human subject), the composition exhibits one or more of: (i) a 5-FC $C_{max}$ of between about 2.0 µg/ml and about 10.0 µg/ml (e.g., between about 2.0-9.5 µg/ml, between about 3.0-8.0 µg/ml, between about 3.0-6.0 µg/ml, between about 3.5-8.0 µg/ml, or between about 2.5-4.5 µg/ml); (ii) a $t_{median}$ of about 3 hrs or greater, (e.g., between about 3-12 hrs, between about 3-10 hrs, between about 4-12 hrs, between about 4-10 hrs, between about 5-12 hrs, between about 5-10 hrs, between about 6-12 hrs, or between about 6-10 hrs, or between about 6-8 hrs); (iii) an AUC of about 20-80 µg*hr/ml (e.g., between about 25-75 µg*hr/ml, between about 30-70 µg*hr/ml, between about 30-65 µg*hr/ml, between about 30-60 µg*hr/ml, or between about 35-65 µg*hr/ml); and (iv) a $t_{1/2}$ of between about 3-8 hrs (e.g., between about 3-7 hrs, between about 4-8 hrs, or between about 4-7 hrs).

The disclosure provides an oral extended release formulation comprising 5-Fluorocytosine (5-FC), wherein said formulation provides enhanced bioavailability with food and wherein upon administration the ratio of the AUC in the fed state over the AUC in the fasted state has a value selected from the group consisting of: (i) about 1.5 to about 3.0; (ii) about 1.8 to about 2.5; and (iii) about 1.9 to about 2.3. In one embodiment, the formulation further comprises at least one hydrophilic matrix forming polymer (e.g., one or more of carbopol, polyvinyl acetate and povidone based polymer, hydroxypropyl cellulose (HPC), hydroxymethyl cellulose (HPMC), and polyethylene oxide (PolyOx)). In yet another embodiment, the hydrophilic matrix forming polymers make up about 10 weight percent to about 40 weight percent of the composition. In a further embodiment, 5-FC is present in an amount of about 100 mg to about 2000 mg. In yet another embodiment, the hydrophilic polymers make up about 10 weight percent to about 40 weight percent of the composition and 5-FC is present in an amount of about 100 mg to about 2000 mg. In one embodiment, the composition exhibits a 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

The disclosure also provides an oral extended release formulation comprising 5-Fluorocystosine wherein upon administration the ratio of $C_{max}$ fed/$C_{max}$ fasted has a value selected from the group consisting of (i) about 1.5 to about 3.0 and (ii) about 1.8 to about 2.4. In one embodiment, the formulation further comprises at least one hydrophilic matrix forming polymer (e.g., one or more of carbopol, polyvinyl acetate and povidone based polymer, hydroxypropyl cellulose (HPC), hydroxymethyl cellulose (HPMC), and polyethylene oxide (PolyOx)). In yet another embodiment, the hydrophilic matrix forming polymers make up about 10 weight percent to about 40 weight percent of the composition. In a further embodiment, 5-FC is present in an amount of about 100 mg to about 2000 mg. In yet another embodiment, the hydrophilic polymers make up about 10 weight percent to about 40 weight percent of the composition and 5-FC is present in an amount of about 100 mg to about 2000 mg. In one embodiment, the composition exhibits a 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

The disclosure also provide an oral extended release formulation comprising 5-Fluorocytosine wherein said formulation provides enhanced bioavailability with food and wherein upon administration the $AUC_{0-inf}$ in the fed state is greater than about 70% of the AUC in the fasted state of flucytosine immediate release. In one embodiment, the formulation further comprises at least one hydrophilic matrix forming polymer (e.g., one or more of carbopol, polyvinyl acetate and povidone based polymer, hydroxypropyl cellulose (HPC), hydroxymethyl cellulose (HPMC), and polyethylene oxide (PolyOx)). In yet another embodiment, the hydrophilic matrix forming polymers make up about 10 weight percent to about 40 weight percent of the composition. In a further embodiment, 5-FC is present in an amount of about 100 mg to about 2000 mg. In yet another embodiment, the hydrophilic polymers make up about 10 weight percent to about 40 weight percent of the composition and 5-FC is present in an amount of about 100 mg to about 2000 mg. In one embodiment, the composition exhibits a 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm. In yet another embodiment, the AUC in the fed state is less than about 125% of the AUC in the fasted state of flucytosine immediate release. In yet a further embodiment, the AUC in the fed state is about 80-100% of the AUC in the fasted state for flucytosine immediate release. In yet a further embodiment, the AUC in the fed state is about 83-95% of the AUC in the fasted state for flucytosine immediate release.

The disclosure also provides an oral extended release formulation comprising 5-Fluorocytosine wherein upon administration the $C_{max}$ in the fed state is less than about 90% of the $C_{max}$ in the fasted state of flucytosine immediate release. In one embodiment, the $C_{max}$ in the fed state is greater than about 30% of the $C_{max}$ in the fasted state of flucytosine immediate release. In yet a further embodiment, the $C_{max}$ in the fed state is about 50-85% of the $C_{max}$ in the fasted state for flucytosine immediate release. In one embodiment, the formulation further comprises at least one hydrophilic matrix forming polymer (e.g., one or more of carbopol, polyvinyl acetate and povidone based polymer, hydroxypropyl cellulose (HPC), hydroxymethyl cellulose (HPMC), and polyethylene oxide (PolyOx)). In yet another embodiment, the hydrophilic matrix forming polymers make up about 10 weight percent to about 40 weight percent of the composition. In a further embodiment, 5-FC is present in an amount of about 100 mg to about 2000 mg. In yet another embodiment, the hydrophilic polymers make up about 10 weight percent to about 40 weight percent of the composition and 5-FC is present in an amount of about 100 mg to about 2000 mg. In one embodiment, the composition exhibits a 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

The disclosure provides a method of treating a fungal infection by administering a modified release formulation (e.g., a monolithic solid tablet) of the disclosure.

The disclosure also provides a method of treating cancer, infectious disease or other disease in a mammal by administering a pharmaceutical composition of the disclosure in conjunction with a polypeptide comprising cytosine deaminase activity to treat cancer in a mammal. In one embodiment, the polypeptide is local to the cancer or tumor (e.g., the polypeptide is not systemically or widely distributed in a subject).

The disclosure provides a method of treating cancer, infectious disease or other disease in a mammal by administering a pharmaceutical composition formulation of the disclosure in conjunction with a polynucleotide encoding a cytosine deaminase to treat cancer in a mammal. In this context a polynucleotide can be comprised of natural or synthetic nucleotides, can be an oligonucleotide, can be RNA or DNA, and can be single or double stranded. In one aspect, the polynucleotide is delivered using a gene delivery system (GDS). A gene delivery system is any procedure or formulation that can deliver a heterologous polynucleotide to target cancer cells or other diseased or disease-associated cells. Examples of gene delivery systems are: a polynucleotide alone delivered by injection, with an inert carrier such as gold particles, by electroporation, by hydrodynamic stress, sonoporation or other physical methods; as a polynucleotide formulated with a synthetic non-viral delivery system and delivered by various routes such as injection or infusion, all of which are well-known to those in the art (see, e.g., Li and Huang, Gene Therapy, 13:1313-1319, 2006). The GDS can deliver a polynucleotide or polynucleotides to cells of a tumor, other diseased cells or disease associated cells in a mammal before dosing with a pharmaceutical composition of the disclosure. In another aspect, the polynucleotide encoding a cytosine deaminase is delivered with a GDS that is a bacterium such as various *Salmonella, Clostridium* or *Listeria* bacterial types that are known to be capable of infecting tumors or diseased tissue. In another aspect, the polynucleotide encoding a cytosine deaminase is delivered with a GDS that is a viral or viral derived vector. The viral vector can be replicating or non-replicating, can be delivered as a viral particle or as polynucleotide(s) encoding the viral vector, and can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., *Concepts in Genetic Medicine*, ed. Boro propulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000 and *Gene Therapy Therapeutic Mechanism and Strategies*, ed. Nancy Smyth Templetone and Danilo D Lasic, Marcel Dekker, Inc., New York, N.Y., 2000; the disclosures of which are incorporated herein by reference).

In one embodiment, the viral vector can be a replication competent retroviral vector capable of infecting only replicating mammalian cells. Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosure of which are incorporated herein by reference). The replication competent retroviral vector can comprise an Orthoretrovirus or more typically a gamma retrovirus vector.

In one aspect, a replication competent retroviral vector comprises an internal ribosomal entry site (IRES) 5' to the polynucleotide encoding a cytosine deaminase. In one embodiment, the polynucleotide encoding a cytosine deaminase is 3' to an ENV polynucleotide of a retroviral vector.

In another embodiment, a method of treating a fungal disease is provided. The method comprises administering to a subject in need thereof a fungus-treating effective amount of a sustained-release formulation comprising 5-fluorocytosine.

In yet another embodiment, a method of treating a cancer is provided. The method comprises administering to a subject in need thereof a sufficient amount of an expression vector to induce expression of a cytosine deaminase which deaminates 5-FC to 5-fluorouracil (5-FU) in cancer cells and a cancer-treating effective amount of an extended release formulation comprising 5-fluorocytosine, such that the serum levels of between about 1-200 µg/ml are achieved (e.g., between about 30-120, 20-90 µg/ml, 30-80 µg/ml, and typically about 40-70 µg/ml). It is to be understood that any value between about 1-200 µg/ml is contemplated by the disclosure. In one embodiment, the serum levels of 5-FC are obtained using an extended release formulation of the disclosure administered 1-4 times per day (about 50-250 mg/kg/day). In a further embodiment, the dose is administered one time per day at 50-200 mg/kg, 2 times per day at 25-100 mg/kg, three times per day at about 16-67 mg/kg, or four times per day at 12-50 mg/kg. Again it will be recognized that any dose between 1-200 (e.g., 10-100) mg/kg per day can be included, the dosing schedule adjusted to achieve the desired amount and serum levels. In one embodiment, the 5-FC formulation of the disclosure is used to treat a subject for 7 days out of every month for months or years. In another embodiment, the dose can be from about 1 to 5 g administered 3-4 doses per day. In yet another embodiment, the 5-FC formulation of the disclosure is administered from about 2 to 8 g (e.g., 6-7 g) 2 or more times per day. In one aspect, the dose of 5-FC is adjusted based upon the activity of cytosine deaminase activity within a subject, tissue or cell. For example, polynucleotides can be generated that provide more effective transcription or translation or increased cytosine deaminase activity. In such instances a lower dose of 5-FC can be provided to a subject to achieve an effective treating amount of 5-FC compared to a subject that receives a standard or less effective cytosine deaminase.

In another embodiment, the disclosure provides a method of treating a subject having infected cells, or other diseased cells such as a cell proliferative disorder. The method comprises: a) contacting the subject with a therapeutically effective amount of a replication competent retrovirus comprising: a nucleic acid sequence encoding a retroviral GAG protein; a nucleic acid sequence encoding a retroviral POL protein; a nucleic acid sequence encoding a retroviral envelope; a retroviral polynucleotide sequence comprising Long-Terminal Repeat (LTR) sequences at the 5' or 3' or 5' and 3' end of the retroviral (e.g. an Orthoretroviral) polynucleotide sequence or a heterologous promoter sequence; a cassette comprising an internal ribosome entry site (IRES) operably linked to a heterologous nucleic acid sequence encoding a polypeptide comprising cytosine deaminase activity, wherein the cassette is positioned 5' to the 3' LTR sequence and/or 3' to the sequence encoding the retroviral envelope; and cis-acting sequences for reverse transcription, packaging and integration in a target cell; b) administering to the subject an effective amount of 5-FC that is converted into a toxic drug by a cytosine deaminase at the site of a cell proliferative disorder (e.g., a brain cancer, lung cancer, colon-rectum cancer, breast cancer, prostate cancer, urinary tract cancer, uterine cancer lymphoma, oral cancer, pancreatic cancer, leukemia, melanoma, stomach cancer and ovarian cancer, an HIV infected cell population, other virally or bacterially infected cell population, or an autoimmune cell population). In another embodiment, the replication competent retrovirus can contain a tissue specific promoter (e.g., a probasin, recombinant probasin or androgen response promoter such as a dual-androgen response element promoter) making the retrovirus capable of only replicating in cells in which that promoter is active. In another embodiment the replication competent retrovirus does not include an IRES element. In another embodiment, the replication competent retrovirus can contain a microRNA target sequence making the retrovirus capable of only or predominantly replicating in cells which are cancerous. In another embodiment the retrovirus is tissue specific by inclusion of "target" sequences for miRNA's that are specific to certain tissues such as hematopoietic cells, liver cells or muscle cells. (Bell and Kirin, Nature Biotech., 26:1347, 2008, incorporated herein by reference) so that the virus does not express in these tissues. Alternatively the virus can include a target that is expressed ubiquitously but is low in tumor cells, such as let-7.

The disclosure provides compositions and methods for treating a cancer, infectious disease, hyperproliferative disease or fungal disease. In one embodiment, the method includes at least a first loading dose of 5-FC sufficient to obtain a serum concentration of about 1-200 (e.g., 10-100) µg/ml within 1-2 days and a plurality of extended release doses of 5-FC sufficient to maintain a serum concentration of about 1-200 µg/ml. The plurality of extended release doses are typically administered to obtain peak blood levels of 5-FC between about 1-200 µg/ml (e.g., between about 30-120 µg/ml, 20-90 µg/ml, 30-80 µg/ml, and typically about 40-70 µg/ml). It is to be understood that any value between about 1-200 µg/ml is contemplated by the disclosure. In one embodiment, the serum levels of 5-FC are obtained using a dose formulation of the disclosure administered 1-4 times per day (about 50-250 mg/kg/day given in divided doses). In a further embodiment, the dose is administered 1 time per day at about 50-200 mg/kg, two times per day at about 25-100 mg/kg, three times per day at about 16-67 mg/kg, or four times per day at about 12-50 mg/kg. Again it will be recognized that any dose between 1-250 (e.g., 10-100) mg/kg per day can be included, the dosing schedule adjusted to achieve the desired amount and serum levels. In another embodiment, the plurality of extended release doses maintains a serum concentration of 75%-125% of the area under the curve of the steady state level or the first loading dose.

The details of one or more embodiments of the disclosure are set forth in the accompanying drawings and the description below. Other features, objects, and advantages will be apparent from the description and drawings, and from the claims.

DETAILED DESCRIPTION

Figure 1A:
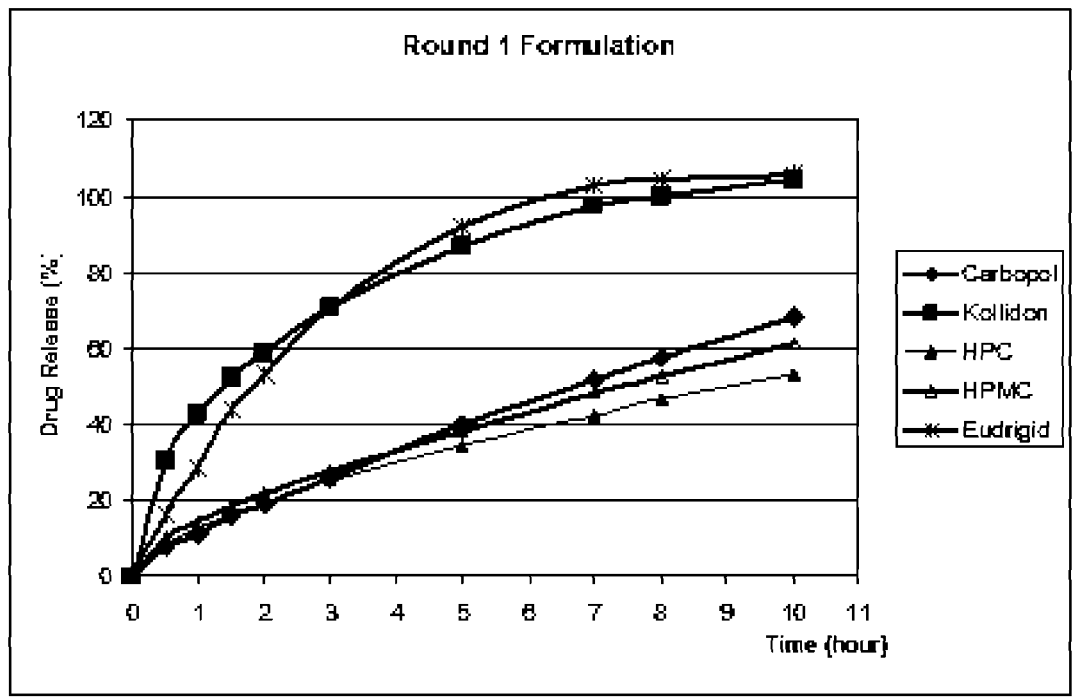
FIG. 1A-D shows the dissolution rates of prototypes formulations in pH 7 dissolution media.
Figure 1B:
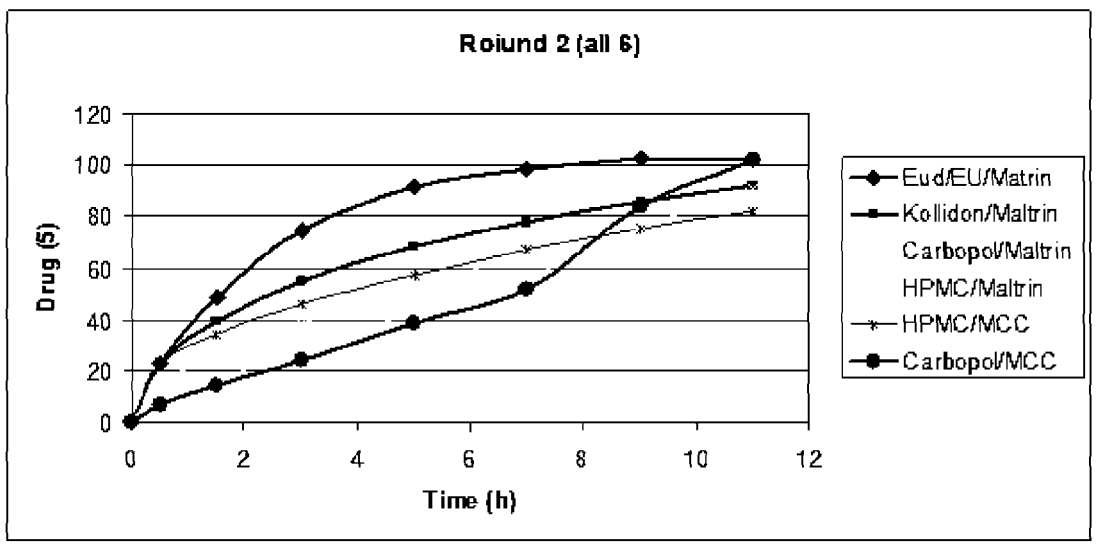
Figure 1C:
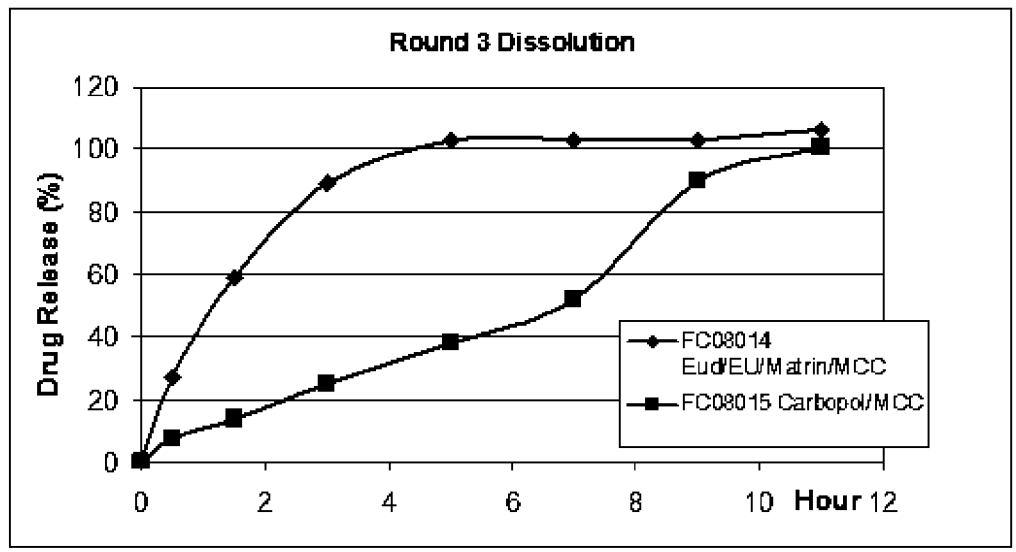
Figure 1D:
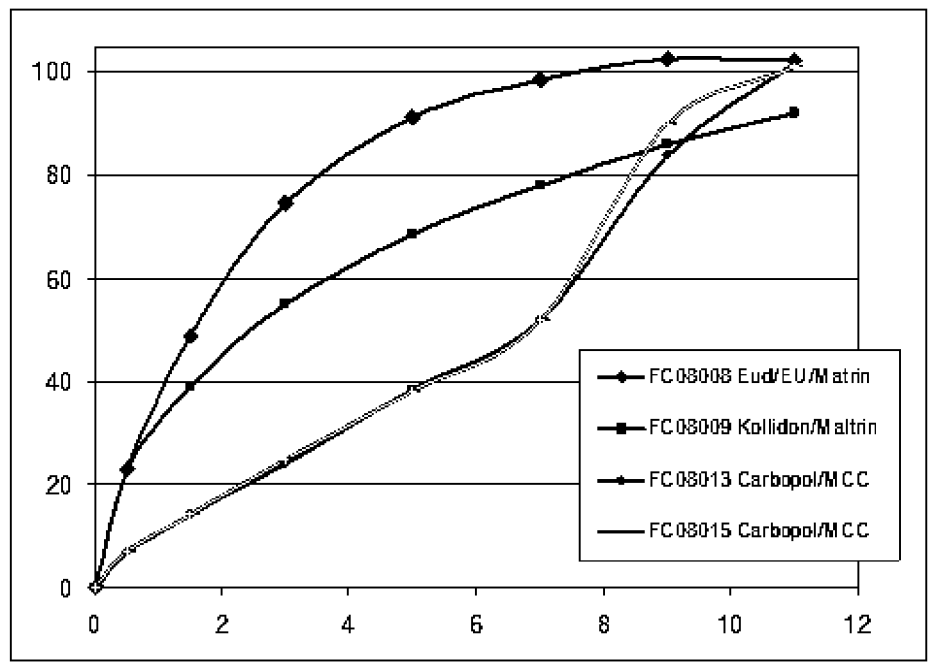

As used herein and in the appended claims, the singular forms "a," "and," and "the" include plural referents unless the context clearly dictates otherwise. Thus, for example, reference to "an agent" includes a plurality of such agents and reference to "the cancer cell" includes reference to one or more cancer cells, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

The term area under the curve (AUC) refers to a plot of concentration of drug in plasma versus time. AUC is usually given for the time interval zero to infinity. The AUC (from zero to infinity) represents the total amount of drug absorbed by the body, irrespective of the rate of absorption. This is useful when trying to determine whether two formulations of the same dose release the same dose of drug to the body. The AUC of a non-sustained release dosage form compared to that of an extended release dosage serves as the basis for a measurement of bioavailability.

The term "percent bioavailability" represents the fraction of drug absorbed from an extended release formulation as compared to the same drug delivered in a non-sustained release form. It is typically calculated from the $AUC_\infty$ of the extended release formulation versus the $AUC_\infty$ for the same drug in a non-sustained release formulation.

The term "prodrug" as used in this application refers to a precursor or derivative form of a pharmaceutically active substance that is less cytotoxic to cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986); Stella et al., "Prodrugs: A Chemical Approach to Targeted Drug Delivery," Directed Drug Delivery, Borchardt et al., (ed.), pp. 247-267, Humana Press (1985); and Dachs et al. "From bench to bedside for gene-directed enzyme prodrug therapy of cancer" Anticancer Drugs 16:349-359 2005. The prodrugs of this disclosure include, but are not limited to, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this disclosure include, but are not limited to, those chemotherapeutic agents described above.

Any compound that will be converted in vivo to provide a biologically, pharmaceutically or therapeutically active form of 5-FC of the disclosure is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). Examples of prodrugs of 5-FC include, but are not limited to, 5-fluorocytidine-monophosphate, diphosphate, or triphosphate; 5-fluorocytidine; 5-fluoro-2' deoxyfluorocytosine; or cytidine or a cytidine with 1, 2 or 3 phosphates. Photoactivatable 5-FC, salts or esters thereof are also contemplated. Such photoactivatable compounds can comprise a photosensitive linker that is cleavable upon irradiation with, for example, a UV light (including lights implanted within a tumor site that can be remotely or temporally activated).

The term "$C_{max}$" as used herein means the maximum observed plasma concentration following administration of a drug.

The term "$T_{max}$" as used herein means the time point of maximum observed plasma concentration.

The term "$T_{median}$" as used herein means the time point when a ½ of AUC is reached.

The plasma half-life of a drug ($T_{1/2}$) is the time necessary to halve the plasma concentration, for example to decrease from 100 to 50 mg/L.

Sustained-release or slow-release (SR), extended-release (ER, XR, or XL), time-release or timed-release, controlled-release (CR), or continuous-release (CR) pills are tablets or capsules formulated to dissolve slowly and release a drug over time. In this application the terms "sustained release" or "extended release" describes all of these types of formulations. The advantages of sustained-release tablets or capsules are that they can often be taken less frequently than instant-release formulations of the same drug, and that they provide levels of the drug in the bloodstream that are fairly even. Sustained-release tablets and formulations are formulated so that the active ingredient is embedded or encapsulated in a matrix of insoluble substance or in vesicular compartments so that the dissolving drug is slowly delivered from the matrix or delivered by vesicle compartmental disruption or degradation. In some SR formulations the matrix physically swells up to form a gel, so that the drug has first to dissolve in the matrix, then exit through the outer surface.

Currently marketed 5-FC is an immediate release capsule formulation (Ancobon®, 250 mg and 500 mg capsules) which has a half life of 2.4-4.8 hours in the blood stream after oral dosing. This necessitates dosing patients 4× per day (QID) to maintain therapeutic levels. The known therapeutic levels are recommended to be 30-80 μg/ml in serum for criptococcal infection (or 40-60 μg/ml for *Candida*) 2 h post dosing during chronic dosing (this is the peak concentration). Toxicity occurs generally if 100 μg/ml is exceeded (Vermes et al., Chemotherapy, pp. 86-94, 2000).

The pharmacokinetics of 5-FC have been investigated and reviewed extensively. 5-FC is absorbed very rapidly and almost completely: 76-89% is bioavailable after oral administration. In patients with normal renal function, peak concentrations are attained in serum and other body fluids within 1-2 hours. Because of its small size and water solubility and the fact that it is not bound by serum proteins to a great extent, 5-FC is rapidly cleared in the kidneys. 5-FC is only minimally metabolized in the liver. Renal elimination is via glomerular filtration; no tubular resorption or secretion takes place. The half-life of 5-FC in the serum is about 2-5 h in patients with normal renal function, but can be extended up to 85 h in patients with severe renal insufficiency.

Bioavailability following oral administration has been estimated by comparing the area under the curve of serum concentrations after oral and intravenous administration. The results showed 76% to 89% absorption by oral administration. Peak serum concentrations of 30 to 40 µg/ml have been reached within 2 hours of administration of a 2 gram oral dose to normal subjects. Other studies revealed mean serum concentrations of approximately 70 to 80 µg/ml, 1 to 2 hours after a dose in patients with normal renal function receiving a 6-week regimen of 5-FC (150 mg/kg/day given in divided doses every 6 hours) in combination with amphotericin B. Most 5-FC is excreted via the kidneys by means of glomerular filtration without significant tubular reabsorption. 5-FC is deaminated (in the absence of heterologous viral vectors of the disclosure) by gut bacterial cytosine deaminase to 5-fluorouracil. The area under the curve (AUC) ratio of 5-fluorouracil to 5-FC is about 4%.

The half-life of 5-FC is prolonged in patients with renal insufficiency; the average half-life in nephrectomized or anuric patients was 85 hours (range: 29.9 to 250 hours). A linear correlation was found between the elimination rate constant of 5-FC and creatinine clearance. In adult patients with a creatinine clearance of >40 mL/min, a standard dose of 37.5 mg/kg every 6 h of IR 5-FC is typically used. If the creatinine clearance is between 20 and 40 mL/min, the recommended dose is 37.5 mg/kg every 12 h. In patients with a creatinine clearance of <20 mL/minute, the dose of 5-FC is about 37.5 mg/kg once daily.

In vitro studies have shown that 2.9% to 4% of 5-FC is protein-bound over the range of therapeutic concentrations found in the blood. 5-FC readily penetrates the blood-brain barrier, achieving clinically significant concentrations in cerebrospinal fluid.

Accordingly, conventional therapy with 5-fluorocytosine requires high daily dosing due to the rapid clearance of the drug from the body. Typical conventional dosing for humans is about 8 grams of 5-fluorocytosine per day, generally taken in equal doses 4 times per day (e.g., about 2 grams per dose and this dose taken as about 250 mg every 15 minutes, to avoid nausea). Compliance by subjects in need of such treatment of fungal infection or in combination with cancer therapies is difficult to achieve.

The disclosure provides compositions including 5-FC in a formulation for extended release (a 5-FC-SR; used interchangeably with 5-FC-ER or 5-FC-XR). The 5-FC-ER composition includes at least one hydrophilic compound, at least one binder, and at least one pharmaceutical diluent. The 5-FC-ER provides one or more of the following characteristics when administered to a fed human subject in a single 500 mg FC dose: (i) a 5-FC $C_{max}$ of between about 2.0 µg/ml and about 10.0 µg/ml (e.g., between about 2.0-9.5 µg/ml, between about 3.0-8.0 µg/ml, between about 3.0-6.0 µg/ml, between about 3.5-8.0 µg/ml, or between about 2.5-4.5 µg/ml); (ii) a $t_{median}$ of about 3 hrs or greater, (e.g., between about 3-12 hrs, between about 3-10 hrs, between about 4-12 hrs, between about 4-10 hrs, between about 5-12 hrs, between about 5-10 hrs, between about 6-12 hrs, or between about 6-10 hrs, or between about 6-8 hrs); (iii) an AUC of about 20-80 µg*hr/ml (e.g., between about 25-75 µg*hr/ml, between about 30-70 µg*hr/ml, between about 30-65 µg*hr/ml, between about 30-60 µg*hr/ml, or between about 35-65 µg*hr/ml); and (iv) a $t_{1/2}$ of between about 3-8 hrs (e.g., between about 3-7 hrs, between about 4-8 hrs, or between about 4-7 hrs). In one embodiment, the formulation upon administration to a fed subject remains in the stomach for between about 4 to about 8 hours.

The 5-FC may be homogeneously dispersed in the 5-FC-ER. In some embodiments, the 5-FC is present in the composition in an amount of about 100 mg to about 2000 mg; about 100 mg to about 1500 mg; about 100 mg to about 1200 mg; about 100 mg to about 1000 mg; about 100 mg to about 900 mg; about 100 mg to about 800 mg; about 100 mg to about 700 mg; about 100 mg to about 600 mg; about 100 mg to about 500 mg; or about 100 mg to about 250 mg. In some embodiments, the 5-FC is present in the composition in an amount of about 200 mg to about 2000 mg. In another embodiment, the 5-FC is present in the composition in an amount of about 250 mg, 500 mg, 750 mg, 1000 mg, 1250 mg, 1500 mg, 1750 mg or 2000 mg.

In one embodiment, at least one hydrophilic compound is present in the 5-FC-ER in an amount of about 5% to about 40% by weight; the at least one binder is present in the 5-FC-ER in an amount of about 0.5% to about 30% by weight; and the at least one pharmaceutical diluent is present in the 5-FC-ER in an amount of about 10% to about 40% by weight. In another embodiment, the at least one hydrophilic compound is present in the 5-FC-ER in an amount of about 8% to about 31% by weight; the at least one binder is present in the 5-FC-ER in an amount of about 5% to about 25% by weight; and the at least one pharmaceutical diluent is present in the 5-FC-ER in an amount of about 15% to about 30% by weight. In another embodiment, the at least one hydrophilic compound is present in the 5-FC-ER in an amount of about 10% to about 20% by weight; the at least one binder is present in the 5-FC-ER in an amount of about 10% to about 25% by weight; and the at least one pharmaceutical diluent is present in the 5-FC-ER in an amount of about 15% to about 30% by weight. In some embodiments, the at least one hydrophilic compound is present in the 5-FC-ER in an amount of about 80, about 90, about 100, about 110, about 120, about 130, about 140, about 150, about 160, about 170, about 180, about 190, about 200, about 220, about 240, about 260, about 280, or about 30% by weight; the at least one binder is present in the 5-FC-ER in an amount of about 40, about 50, about 60, about 70, about 80, about 90, about 100, about 110, about 120, about 130, about 140, about 150, about 160, about 170, about 180, about 190, about 200, or about 220, by weight; and the at least one pharmaceutical diluent is present in the 5-FC-ER in an amount of about 100, about 200, about 30% or about 40% by weight. In one embodiment, the at least one hydrophilic compound is present in the 5-FC-ER in an amount of about 80, about 120, or about 20% by weight; the at least one binder is present in the 5-FC-ER in an amount of about 50, about 100, or about 15% by weight; and the at least one pharmaceutical diluent is present in the 5-FC-ER in an amount of about 100, about 250, about or 30% by weight.

The 5-FC-ER includes at least one hydrophilic compound. The hydrophilic compound forms a gel matrix that releases the 5-FC at a sustained rate upon exposure to liquids. The rate of release of the 5-FC from the gel matrix depends on the drug's partition coefficient between the components of the gel matrix and the aqueous phase within the gastrointestinal tract. In the compositions of the disclosure, the weight ratio of 5-FC to hydrophilic compound is generally in the range of about 2:1, about 3:1, about 4:1, about 5:1 or about 6:1.

The hydrophilic polymeric matrix forming compound is any compound known in the art to be hydrophilic. Exemplary hydrophilic compounds include without limitation gums, cellulose ethers, acrylic resins, polyvinyl pyrrolidone, protein-derived compounds, and mixtures thereof. Exemplary gums include without limitation heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include without limitation hydroxyalkyl celluloses and carboxyalkyl celluloses. In some embodiments, cellulose ethers include hydroxyethyl celluloses, hydroxypropyl celluloses, hydroxypropylmethyl-celluloses, carboxy methylcelluloses, and mixtures thereof. Exemplary acrylic resins include without limitation polymers and copolymers of acrylic acid, methacrylic acid, methyl acrylate and methyl methacrylate. In some embodiments, the hydrophilic compound is a gum. In other embodiments, the hydrophilic compound is a heteropolysaccharide gum. In further embodiments, the hydrophilic compound is a xanthan gum or derivative thereof. Derivatives of xanthan gum include without limitation, for example, deacylated xanthan gum, the carboxymethyl esters of xanthan gum, and the propylene glycol esters of xanthan gum. In specific embodiments, the hydrophilic polymeric matrix forming compound is Carbomer (e.g., Carbopol-71G), Kollidon SR or a combination thereof.

In another aspect, the 5-FC-ER further includes at least one binder. In one embodiment, the binder is a compound that is capable of cross-linking the hydrophilic compound to form a gel matrix in the presence of liquids. As used herein, "liquids" includes, for example, gastrointestinal fluids and aqueous solutions, such as those used for in vitro dissolution testing. The 5-FC-ER generally includes the binder in an amount of about 3% to about 20% by weight. In one embodiment, the 5-FC-ER generally includes the binder in an amount of about 3% to about 10% by weight. In some embodiments, the at least one binder is present in the 5-FC-ER in an amount of about 3%, about 4%, about 5%, about 6%, about 7%, about 8%, about 9%, about 10%, about 11%, about 12%, or about 13% by weight. In one embodiment, the 5-FC-ER includes the binder in an amount of about 6% to about 7% by weight (and any number there between).

Exemplary binders include homopolysaccharides. Exemplary homopolysaccharides include without limitation galactomannan gums, such as guar gum, hydroxypropyl guar gum, hydroxypropylcellulose (HPC; e.g., Klucel EXF) and locust bean gum. In other embodiments, the binder is an alginic acid derivative, HPC or microcrystallized cellulose (MCC).

In some embodiments, when the 5-FC-ER includes at least one hydrophilic compound and at least one binder, the weight ratio of hydrophilic compound to binder is from about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, or about 1:2 to about 2:1.

When the 5-FC-ER includes at least one hydrophilic compound and at least one binder, the weight ratio of the 5-FC to the sum of the at least one hydrophilic compound and the at least one binder is from about 1:1 to about 12:1, from about 1:1 to about 4:1, from about 1:1 to about 3:1, or from about 1:1 to about 2:1.

The 5-FC-ER may further include one or more pharmaceutical diluents known in the art. Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Non-limiting examples of water-soluble pharmaceutical diluents include lactose, dextrose, sucrose, or mixtures thereof. In other embodiments, the pharmaceutical diluent is water-insoluble. Non-limiting examples of water-insoluble pharmaceutical diluents include dicalcium phosphate or tricapcium phosphate. In some embodiments, the weight ratio of pharmaceutical diluent to hydrophilic compound is generally from about 1:1 to about 4:1, from about 1:1 to about 3:1, from about 1:1 to about 2:1 and any ranges there between. In some embodiments, the weight ratio of pharmaceutical diluent to hydrophilic compound is generally from about 1:1 to about 2:1.

In some embodiments, the 5-FC-ER generally includes one or more pharmaceutical diluents in an amount of about 15% to about 30%. In some embodiments, the 5-FC-ER includes one or more pharmaceutical diluents in an amount of about 15%, about 20%, about 25%, or about 30% by weight.

In other embodiments, a coating, e.g., Opadry®, may be added to the compositions described herein although it is not a requirement.

In some embodiments, the compositions described herein further include a second hydrophilic compound.

The extended release formulations of 5-FC are orally administrable solid dosage formulations. Non-limiting examples of oral solid dosage formulations include matrix tablets, barrier-coated tablets, and tablets and capsules including a plurality of granules. In some embodiments, tablets have a hydrophilic coating.

For most active drug ingredients, there is a therapeutic concentration of the active drug that must be reached in a target tissue, if the desired therapeutic effect is to occur. A extended release pharmaceutical dosage form generally makes an active drug ingredient available for absorption and/or use in the patient's body a little bit at a time over an extended period of time. If the active drug is metabolized or otherwise eliminated by the patient's body, it may be a long time before the drug ingredient reaches such minimum therapeutic concentration in the target tissue(s) of the patient. In order to overcome this, it can be useful to provide an initial rapid release dose of the active drug ingredient to rapidly achieve such minimum therapeutic concentration. Once such minimum therapeutic concentration is surpassed in the target tissue(s), the extended release dosage form can maintain it by delivering the active drug ingredient in sufficient quantities to compensate for the amount of active drug which is metabolized or otherwise eliminated from the target tissue(s).

Another embodiment of the disclosure is a combination extended release/rapid release pharmaceutical capsule which can provide both the rapid release of the active drug ingredient in order to quickly achieve the minimum therapeutic concentration of the active drug in the target tissue(s) of a patient, along with an extended release dose of the active drug ingredient in order to retain such minimum therapeutic concentration or greater in the target tissue(s) over an extended period. The rapid release portion of this combination extended release/rapid release capsule of the disclosure can be achieved by including a separate intact dosage unit form for the rapid release portion in the capsule shell, e.g. a pellet, tablet, small capsule, and the like.

In one embodiment, the extended release/rapid release pharmaceutical tablets or capsules for oral administration of the disclosure may comprise at least two layers: (1) a first layer of a first particulate mixture, said first particulate mixture being the same as the extended release composition described hereinabove; and (2) a second layer of a second particulate mixture comprising the same active drug ingredient as in said first particulate mixture. The first layer of the combination extended release/rapid release pharmaceutical tablets provides an extended release of the active drug ingredient in the same manner as for the extended release pharmaceutical compositions described hereinabove. A second layer provides a rapid release portion of the active drug ingredient by providing a second particulate mixture comprising the active drug ingredient, the second particulate mixture being formulated such that it rapidly disperses upon dissolution of layer in the gastrointestinal tract. The second mixture is a mixture of the active drug ingredient and one or more pharmaceutical carriers formulated to achieve such rapid dispersion in the gastrointestinal tract.

The combined extended release/rapid release tablets of the disclosure can provide, in a dosage unit form, a rapid release of one active drug ingredient and an extended release of a second active drug ingredient, if desired, by incorporating different active drug ingredients in the first and second particulate mixtures described hereinabove.

The combination extended release/rapid release tablet of the disclosure is made such that it dissolves in the portion of the gastrointestinal tract where the active drug ingredient of the rapid release (second particulate) mixture is readily utilized, absorbed, or otherwise transported to the target tissue(s) where its activity is utilized.

The tablet or capsule can comprise a multilayer design. In some embodiment, the 5-FC compositions and formulations may include an immediate release layer and an extended release layer in a tablet or capsule. Such a combination of and IR/ER therapy would be useful for improving the 5-FC profile. The 5-FC present in the immediate release layer is generally present in an amount ranging from about 1 mg to about 500 mg (e.g., about 200 mg).

In some embodiments, the multilayer dosage form further includes a pharmaceutical disintegrant. The disintegrant promotes the dissolution and absorption of 5-FC from the immediate release layer. Non-limiting examples of pharmaceutical disintegrants include croscarmellose sodium, starch glycolate, crospovidone, and unmodified starch. In one embodiment, the disintegrant is in the first layer (i.e., the immediate release layer), of the dosage form.

In some embodiments, the multilayer tablets of the disclosure are prepared by first preparing the immediate release layer and extended release layer blends separately. The extended release core tablets are compressed in a usual manner to produce a matrix tablet core or layer. The immediate release layer of the disclosure is prepared by first mixing the 5-FC with one or more diluents (e.g., microcrystalline cellulose). This mix is then optionally mixed with one or more disintegrants. The blend is mixed with magnesium stearate. Finally, the immediate release layer blend and the extended release layer blend are compressed into multi-layer (e.g., bi-layer) tablets. In another embodiment, the immediate release layer can be coated around the extended release core tablet.

When dosed appropriately (e.g., daily administration of 50-250 mg/Kg/day divided and administered 1-4 times for at least 5 half lives), a 5-FC-ER formulation provides mean blood levels of 5-FC between about 1-200 µg/ml (e.g., between about 20-120 µg/ml, 30-80 µg/ml, or about 40-70 µg/ml). It is to be understood that any value between about 1-200 µg/ml is contemplated by the disclosure. In one embodiment, the levels of 5-FC are obtained using an extended release dose formulation of the disclosure administered 1-4 times per day (about 50-200 mg/kg/day). In a further embodiment, the dose is administered one time per day at 50-200 mg/kg, two times per day at 25-100 mg/kg, three times per day at about 16-67 mg/kg, or four times per day at 12-50 mg/kg. Again it will be recognized that any dose between 1-200 (e.g., 10-100) mg/kg per day can be included, the dosing schedule adjusted to achieve the desired amount and serum levels. In one embodiment, the dose of 5-FC is adjusted based upon the activity of cytosine deaminase activity within a subject, tissue or cell.

The disclosure provides an oral pharmaceutical composition comprising 5-FC, wherein the pharmaceutical composition is a modified release form (e.g., a monolithic solid tablet, a pellet, granules and the like) and releases 5-FC into the upper gastrointestinal tract of a subject over a sustained period of time. The composition can further comprise a hydrophilic polymer such as one or more of carbopol (e.g., carbopol 71-G), hydroxypropyl cellulose (HPC), hydroxymethyl cellulose (HPMC), kollidon, and polyethylene oxide (PolyOx). The hydrophilic polymers can make up about 10 weight percent to about 40 weight percent of the composition. In one embodiment, the 5-FC is present in an amount of about 100 mg to about 2000 mg per tablet or dose. In another embodiment, the composition exhibits 5-FC in-vitro dissolution rate of greater than about 80% within about 4 to about 12 hours as measured by the USP Type II dissolution apparatus (paddle method) at 75 rpm in 900 ml DI water at 37° C. using 5-FC USP method with UV detection at about 275 nm. In yet another embodiment, the 5-FC is present in the pharmaceutical composition in an amount of about 500 mg and wherein after oral administration of the composition to a fed subject, the composition exhibits: (i) a 5-FC $C_{max}$ of between about 2.0 µg/ml and about 10.0 µg/ml (e.g., between about 2.0-9.5 µg/ml, between about 3.0-8.0 µg/ml, between about 3.0-6.0 µg/ml, between about 3.5-8.0 µg/ml, or between about 2.5-4.5 µg/ml); (ii) at $t_{median}$ of about 3 hrs or greater, (e.g., between about 3-12 hrs, between about 3-10 hrs, between about 4-12 hrs, between about 4-10 hrs, between about 5-12 hrs, between about 5-10 hrs, between about 6-12 hrs, or between about 6-10 hrs, or between about 6-8 hrs); (iii) an AUC of about 20-80 µg*hr/ml (e.g., between about 25-75 µg*hr/ml, between about 30-70 µg*hr/ml, between about 30-65 µg*hr/ml, between about 30-60 µg*hr/ml, or between about 35-65 µg*hr/ml); and (iv) a $t_{1/2}$ of between about 3-8 hrs (e.g., between about 3-7 hrs, between about 4-8 hrs, or between about 4-7 hrs).

In yet another embodiment, the 5-FC in the pharmaceutical composition wherein after 2 gm oral administration of the pharmaceutical composition to a fed subject, the composition exhibits (i) a 5-FC $C_{max}$ of between about 5 and 80 µg/ml, about 5 and 70 µg/ml, about 5 and 60 µg/ml, about 5 and 50 µg/ml, about 5 and 40 µg/ml, about 5 and 30 µg/ml, or about 5 and about 20 µg/ml, and (ii) a time to maximum ($t_{max}$) of between about 4 and about 10 hours (e.g., 3-7 hours to reach peak release of 5-FC).

Where the formulation comprises both a rapid release and extended/sustained release, the rapid release portion will comprise a $t_{max}$ of about 1-2 hours and the extended release portion will comprise a $t_{max}$ of between 3-12 hours. In methods of treatment comprising a rapid release-extended release combination a therapeutic concentration can be rapidly achieved and sustained over a period of 1-12 hours.

Administration of a 5-FC-ER of the disclosure allows for extended release of 5-fluorocytosine and, therefore, a reduction in the number of doses given per day to 1, 2, or 3 and/or a reduction in the total daily dose, without the need to take a dose in divided portions to avoid nausea or gastrointestinal symptoms. This allows for improved patient compliance with drug therapy and reduced side effects.

In addition, the monolithic formulations described herein and other commonly used slow-release (or sometimes referred to as extended release) carriers and delivery agents are contemplated.

An modified release (extended release) formulation, (e.g., tablet, granule, pellet, capsule or the like) of the disclosure typically comprises about 25, 50, 100, 200, 250, 300, 400, 500, 750, 1000, 1250, 1500, 1750, or 2000 mg of active agent (e.g., 5-FC) per unit dosage form. Where a composition comprises 5-FC and a second active agent (e.g., leukovorin), the amount of active agent for each can be modified to fall with a desired range (e.g., 25-500 mg/composition for each active agent).

In one embodiment, the composition of the disclosure is optimized with a coating to promote absorption in the upper gastrointestinal track including the stomach. Such absorption would prevent metabolism of 5-FC by bacterial cytosine deaminases in the large intestine.

In another aspect, the composition may comprise a siRNA or antisense molecule that specifically inhibits cytosine deaminase expression from a source other than the desired source. Such siRNA or antisense molecules can be readily designed by examining the difference in the coding sequences for cystosine deaminases. For example, where the cytosine deaminase of a replication competent retroviral vector is a humanized cytosine deaminase or a yeast cytosine deaminase an siRNA that specifically inhibits a bacterial cytosine deaminase would prevent unwanted metabolism in the colon by bacteria and fungi in the colon.

The use of the extended release formulation can be in form of a tablet, capsule, trochar, emulsion, suspension, and will vary according to the route of administration selected. For solutions or emulsions, suitable carriers include, for example, aqueous or alcoholic/aqueous solutions, emulsions or suspensions, including saline and buffered media. As described elsewhere herein a pharmaceutical composition of the disclosure may include a conventional additive, such as a stabilizer, buffer, salt, preservative, filler, flavor enhancer and the like, as known to those skilled in the art. Exemplary buffers include phosphates, carbonates, citrates and the like. Exemplary preservatives include EDTA, EGTA, BHA, BHT and the like. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980).

As used herein the term "therapeutically effective amount" means the amount of a prodrug and/or other biological substance necessary to induce a desired pharmacological effect. The amount can vary greatly according to the effectiveness of a particular active substance, the age, weight, and response of the individual host as well as the nature and severity of the host's symptoms. Other factors that can be taken into account include the expression rate of a cytosine deaminase polynucleotide from a vector and the activity of a cytosine deaminase for 5-FC. Accordingly, there is no upper or lower critical limitation upon the amount of the prodrug or active substance. The therapeutically effective amount to be employed in the methods of the disclosure can readily be determined by those skilled in the art.

In another aspect, a method is provided for treating a fungal disease. In one embodiment, the method comprises administering to a subject in need thereof a fungus-treating effective amount of extended release formulation comprising 5-FC (e.g., a Monolithic modified-release dosage forms (MMR) comprising 5-FC with increased gastric residence time). The method can be used to treat any applicable fungal disease, including a fungal disease which is a brain fungal disease, a internal organ fungal disease, vaginal fungal disease, mouth fungal disease foot fungal disease and/or which is an infection by a fungus selected from among *Candida* spp., *Cryptococcus* spp., *Sporothrix* spp., *Aspergillus* spp., *Cladosporium* spp., *Exophila* spp. and *Phialophora* spp.

In treating a fungal disease with an extended release formulation comprising 5-fluorocytosine, it can be beneficial to coadminister another anti-fungal agent. Any appropriate antifungal agent may be coadministered with the 5-fluorocytosine-containing extended release formulation, including amphotericin B and azole antifungals such as fluconazole and itraconazole. Such additional agents may be compartmentalized within the extended release formulation, as part of a modified release form (e.g., layered on or in a monolithic solid) or administered separately.

In another embodiment, a method is provided for treating an infectious disease. The method comprises administering to a subject in need thereof a sufficient amount of an expression vector to induce expression of cytosine deaminase in infected cells, and an infection-treating effective amount of an extended release formulation comprising 5-fluorocytosine. The method can be used to treat any applicable non-fungal infectious disease, including viral, bacterial and mycoplasma based diseases. Examples of such diseases include HIV infection, HBV infection, HCV infection, HPV infection, herpes viral infection, Tuberculosi, *pneumocystis carinii*. As with treatment of fungal diseases, administration of the extended release formulation comprising 5-fluorocytosine allows for extended release of 5-fluorocytosine for treatment of infectious disease and, therefore, a reduction in the number of doses given per day to 1, 2 or 3. Also a reduction in the total daily dose due to enhanced formulation or due to enhanced activity of cytosine deaminase to convert 5-FC to 5-FU can be obtained. This allows for improved patient compliance with drug therapy and reduced side effects. In one embodiment, the dose of 5-FC useful for treating an infectious disease subject, wherein the infected cells of the subject comprises a heterologous cytosine deaminase, can be reduced from 1-1,000 fold compared to the dose used for the treatment of a fungal infection without the cytosine deaminase gene.

In treating an infectious disease with an extended release formulation comprising 5-fluorocytosine, it can be beneficial to coadminister another anti-infectious disease agent. Any appropriate anti-infectuous disease agent may be coadministered with the 5-fluorocytosine-containing extended release formulation, including, but not limited to antibiotics, and antivirals such as valcyclovir, neverapin, anti-HIV drug combos, ribovirin and others. Such additional agents may be compartmentalized within the extended release formulation, layered or administered separately.

In another embodiment, a method is provided for treating a hyperproliferative disease. The method comprises administering to a subject in need thereof a sufficient amount of an expression vector to induce expression of cytosine deaminase in hyperproliferating cells, and a proliferation-treating effective amount of an extended release formulation comprising 5-fluorocytosine. The method can be used to treat any applicable hyperproliferative disease such as various autoimmune disorders including rheumatoid arthritis, Crohn's disease, Chronic obstructive pulmonary disease, benign prostate hyperplasia, and others. As with treatment of fungal diseases, administration of the extended release formulation comprising 5-fluorocytosine allows for extended release of 5-fluorocytosine for treatment of hyperproliferative disease and, therefore, a reduction in the number of doses given per day to 1, 2 or 3. Also a reduction in the total daily dose due to enhanced formulation or due to enhanced activity of cytosine deaminase to convert 5-FC to 5-FU can be obtained. This allows for improved patient compliance with drug therapy and reduced side effects. In one embodiment, the dose of 5-FC useful for treating a hyperproliferative disease subject, wherein the hyperproliferative cells of the subject comprise a heterologous cytosine deaminase, can be reduced from 1-1,000 fold compared to the dose used for the treatment of a hyperproliferative disease without the cytosine deaminase gene.

In treating a hyperproliferative disease with an extended release formulation comprising 5-fluorocytosine, it can be beneficial to coadminister another antiproliferative disease agent. Any appropriate anti-proliferative disease agent may be coadministered with the 5-fluorocytosine-containing extended release formulation, including, but not limited to methotrexate, cyclophosphamide other cancer drugs, leucovorin and steroids. Such additional agents may be compartmentalized within the extended release formulation, (e.g., layered in a monolithic form) or administered separately.

In yet another embodiment, a method is provided for treating a cancer. The method comprises administering to a subject in need thereof a sufficient amount of an expression vector to induce expression of cytosine deaminase in cells of the cancer and a cancer-treating effective amount of an extended release formulation comprising 5-fluorocytosine. The method can be used to treat any applicable cancer, including cancers of the adrenal gland, bladder, bone, bone marrow, brain (e.g., glioblastoma multiforme), breast, cervix, gall bladder, ganglia, gastrointestinal tract (e.g., colon and rectal cancers), heart, kidney, liver, lung, muscle, ovary, pancreas, parathyroid, penile, prostate, salivary glands, skin (e.g., melanoma), spleen, testis, thymus, thyroid, and uterus. Cancers to be treated include solid tumors including metastases to a brain cancer, lung cancer, colon-rectum cancer, breast cancer, prostate cancer, urinary tract cancer, uterine cancer lymphoma, oral cancer, pancreatic cancer, leukemia, melanoma, stomach cancer and ovarian cancer. Also the formulation can be used to treat disease of companion and agricultural animals including dogs. In dogs, brain cancer, lymphomas, mast cell tumors and fibrosarcomas can be treated with the formulation of 5FC with the co-administration of a vector containing a gene for cytosine deaminase. As with treatment of fungal diseases, administration of an extended release formulations comprising 5-fluorocytosine allows for extended release of 5-fluorocytosine for treatment of cancer and, therefore, a reduction in the number of doses given per day to 1, 2 or 3. Also a reduction in the total daily dose due to enhanced formulation or due to enhanced activity of cytosine deaminase to convert 5-FC to 5FU can be obtained. This allows for improved patient compliance with drug therapy and reduced side effects. In one embodiment, the dose of 5-FC useful for treating a cancer subject, wherein the cancer of the subject comprises a heterologous cytosine deaminase, can be reduced from 1-1,000 fold compared to the dose used for the treatment of a cancer without the cytosine deaminase gene.

In treating a cancer with an extended release formulation comprising 5-fluorocytosine, it can be beneficial to coadminister another anti-cancer agent. Any appropriate anti-cancer agent may be coadministered with the 5-fluorocytosine-containing extended release formulation, including, but not limited to leukovorin, busulfan, cis-platin, mitomycin C carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; EGFR inhibitors, such as Iressa® (gefitinib) and Tarceva® (erlotinib); proteosome inhibitors; antibodies, such as campath, Herceptin® (trastuzumab), Avastin® (bevacizumab), or Rituxan® (rituximab); steroids and alkalating agents such as temodar, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine. Such additional agents may be compartmentalized within the extended release formulation (e.g., layered in a monolithic formulation) or administered separately.

The prodrug 5-FC is converted to a cytotoxic drug by the action of enzymes inherent in a microorganism or which have been otherwise recombinantly introduced into an organism. For example, the yeast, or bacterial, cytosine deaminase converts the innocuous antibiotic pro-drug 5-FC into the cytotoxic chemotherapeutic agent 5-fluorouracil (5-FU). Humans (and mammals in general) are not known to have a naturally occurring gene encoding an enzyme with significant cytosine deaminase activity. Yeast and bacterial cytosine deaminase have gained recognition in the treatment of cancers using gene delivery and viral vectors for the delivery of the enzyme followed by treatment with 5-FC, which is then converted by the enzyme to a cytotoxic drug (Miller et al., Can Res 62:773-780 2002; Kievit et al., Can Res 59:1417-1421 1999).

One delivery mechanisms for the treatment of cancer is based upon replication competent retroviral vectors (e.g., a mammalian orthoretrovirusretroviral vectors) comprising a cytosine deaminase located downstream of an internal ribosome entry site (IRES). For example, U.S. Pat. No. 6,899,871 to Kasahara et al. describes a vector useful for the treatment of cell proliferative disorders including brain cancers (the disclosure of U.S. Pat. No. 6,899,871 is incorporated herein by reference).

The cytosine deaminase gene used for transfection of the cancer cells may encode any applicable cytosine deaminase which will catalyze the conversion of 5-fluorocytosine to 5-fluorouracil. The 5-fluorouracil is then converted to 5-fluoro-deoxyuridine monophosphate (FdUMP) (as well as other active metabolites such as 5-FdUTP) inside the cancer cell and results in inhibition of thymidylate synthase or by incorporation of 5-FU into 5-fluorouridine monophosphate (FUMP) 5-FUTP and further into RNA, thereby disrupting RNA structures and processes and, ultimately, leading to cell death. Appropriate cytosine deaminases include those from bacteria and fungi, such as cytosine deaminase from *E. coli* (Huber et al. PNAS 91 8302-8306 1994, *Candida kefyr* (see, e.g., U.S. Pat. No. 7,141,404) or *Saccharomyces cerevisiae* (Kievit et al. op. cit.) as well as improved recombinant cytosine deaminases (e.g., codon-humanized CD's and/or stabilized CD's) can be used.

The expression vector used to transfect the cancer cell with the cytosine deaminase may be any applicable expression vector, including a DNA plasmid, a polynucleotide expression vector formulated with a synthetic agent or agents, a bacterial vector, or a viral vector (e.g., *Concepts in Genetic Medicine*, ed. Boro propulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000 and *Gene Therapy: Therapeutic*

Mechanism and Strategies, ed. Nancy Smyth Templetone and Danilo D Lasic, Marcel Dekker, Inc., New York, N.Y., 2000). In one aspect of the invention, retroviral vectors may be used. Retroviral vectors include a replication competent retroviral vector (see, e.g., U.S. Pat. Nos. 6,410,313 and 6,899,871) and a replication defective retroviral vector (see, e.g., U.S. Pat. Nos. 5,716,826, 5,830,458, 5,997,859, 6,133,029, 6,241,982, 6,410,326, 6,495,349, 6,531,307 and 6,569,679). Transduction of cancer cells may be, for example, by direct injection, implantation or systemic administration of an expression vector with a cytosine deaminase gene. Targeting of cytosine deaminase expression to the cancer cell can be facilitated by including an appropriate tissue specific promoter or microRNA in the expression vector. In another embodiment the retrovirus is tissue specific by inclusion of "target" sequences for miRNA's that are specific to certain tissues such as hematopoietic cells, liver cells or muscle cells. (Bell and Kirin, Nature Biotech., 26:1347, 2008, incorporated herein by reference) so that the virus does not express in these tissues. Alternatively the virus can include a target that is expressed ubiquitously but is low in tumor cells, such as let-7.

The methods described herein can be used in any mammalian species, including human, monkey, cow, sheep, pig, goat, horse, mouse, rat, dog, cat, rabbit, guinea pig, hamster and horse. Humans are preferred.

According to the methods described herein, an extended release formulation comprising 5-fluorocytosine can be administered to the host by an appropriate route, either alone or in combination with another drug. An effective amount of extended release formulation comprising 5-fluorocytosine is administered. An effective amount is an amount sufficient to achieve the desired therapeutic effect under the conditions of administration, such as an amount sufficient to reduce or eliminate a fungal infection, reduce or eliminate a nonfungal infectious disease, or to slow the growth, reduce or eliminate cancer cells or cells of a hyperproliferative disease.

In another embodiment, the dose of a composition comprising 5-FC or 5-FC and leukovorin can be modified based upon cytosine deaminase activity. For example, it is possible to modify cytosine deaminase activity and expression by modifying the type of promoter, microRNA or sequence of the cytosine deaminase. In such embodiments, the dose of 5-FC can be adjusted (e.g., where activity and/or expression are high, the 5-FC dose can be reduced).

In another embodiment, a 5-FC composition of the disclosure is used in combination with a replication competent retrovirus comprising cytosine deaminase; viral titers can be determined from a subject comprising the replication competent retrovirus and the dose of 5-FC modified based upon the number of infectious or transforming units and/or the expression of cytosine deaminase. In yet a further embodiment, the dose of a 5-FC or a 5-FC and leukovorin composition of the disclosure can be determined based upon a tumor size. For example, injection of tumors with a replication competent retrovirus comprising an IRES linked to a cytosine deaminase gene can result in about 75% transduction efficiency after about 49 days of spread. With this information a dosage guideline for treating tumors of larger size, such as those that occur in larger animals, including humans can be determined. For example, a dose of $6 \times 10^3$ pfu in tumors of 1.0-1.5 cm$^3$ volume consistently results in transduction of the majority of cells. In another embodiment, the dose of viral vector is about $10^3$ to $10^7$ transforming units (TU) per gram brain weight. Where the activity of a cytosine deaminase gene and expression are known, a proper dose can be determined and adjusted in an individual subject based upon tumor cells in combination with the number of transforming units.

Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

EXAMPLES

Example 1

Materials.

The materials used to prepare the dosage forms described herein were obtained as follows. Flucytosine (5-FC), USP is purchased from Scinopharm (Taiwan); Carbopol 71-G was purchased from Noveon (Cleveland, Ohio, USA); HPMC, NF (Benecel® MP874, hydroxypropylmethylcellulose) and HPC, NF (Klucel®-HXF, hydroxypropyl cellulose) was purchased from Aqualon (Wilmington, Del., USA); Kollidon®-SR (PVA-PVP co-polymer, polyvinyl acetate and povidone based matrix retarding polymer) was purchased from BASF (Ludwigshafen am Rhein, Rhineland-Palatinate, Germany); Directly compressible Dicalcium Phosphate, NF (Emcompress®) was purchased from JRS Pharma (Patterson, N.Y., USA); Maltodextrin was purchased from Grains Processing Corp. (GPC, Muscatine, Iowa); Magnesium Stearate NF is purchased from Spectrum Chemicals (Gardena, Calif., USA) and directly compressible anhydrous Lactose (DCL-21) is purchased from DMV (Veghel, The Netherlands). Sodium bicarbonate (USP-2 grade) was purchased from Church and Dwight (Princeton, N.J.). Avicel® brand of microcrystalline cellulose-NF is purchased from FMC (Philadelphia, Pa.).

In one embodiment, a monolithic modified-release dosage form (MMR) comprising 5-FC with increased gastric residence time is described. The combination of size and shape along with bioadhesiveness and floatation were used to restrict the MMR to the upper gastrointestinal tract (e.g., the stomach).

Dosage forms were prepared by common tableting methods, according to the following general procedure: Flucytosine (5-FC) and diluent (lactose, microcrystalline cellulose, maltodextrin or dicalcium phosphate) were mixed followed by mixing in a suitably sized blender. Hydrophilic or bioadhesive polymers (Carbopol, HPC, HPMC, PolyOx, and the like) were added and mixed well for at least 15 minutes. If used, magnesium stearate was added and mixed for 3 minutes. The resulting blends were compressed using a ten station semi-automatic tablet press to form a concave with rounded edge tooling shape, giving a slightly flattened caplet shaped tablet. The resulting dosage form was assayed for in vitro dissolution, rate of medium uptake, and bioadhesiveness, as described below.

| Ingredient | mg/dose | % |
|---|---|---|
| Flucytosine (5-FC) | 500 | 58.14% |
| Carbopol (71G) | 150 | 17.44% |
| Dicalcium phosphate | 200 | 23.26% |
| Mg Stearate | 10 | 1.16% |
| Total | 860 | 100.0% |

Example 2

The method above was repeated using the following components:

| Ingredient | mg/dose | % |
|---|---|---|
| Flucytosine (5-FC) | 500 | 58.14% |
| HPMC | 150 | 17.44% |
| Dicalcium phosphate | 200 | 23.26% |
| Mg Stearate | 10 | 1.16% |
| Total | 860 | 100.0% |

Example 3

The method above was repeated using the following components:

| Ingredient | mg/dose | % |
|---|---|---|
| Flucytosine (5-FC) | 500 | 58.14% |
| HPC (Klucel HXP) | 150 | 17.44% |
| Dicalcium phosphate | 200 | 23.26% |
| Mg Stearate | 10 | 1.16% |
| Total | 860 | 100.0% |

Example 4

The method above was repeated using the following components:

| Ingredient | mg/dose | % |
|---|---|---|
| Flucytosine (5-FC) | 500 | 58.14% |
| Kollidone SR | 150 | 17.44% |
| Dicalcium phosphate | 200 | 23.26% |
| Mg Stearate | 10 | 1.16% |
| Total | 860 | 100.0% |

Example 5

The method above was repeated using the following components:

| Ingredient | mg/dose | % |
|---|---|---|
| Flucytosine (5-FC) | 500 | 58.14% |
| Eudragid RLPO | 150 | 17.44% |
| Dicalcium phosphate | 200 | 23.26% |
| Mg Stearate | 10 | 1.16% |
| Total | 860 | 100.0% |

Example 6

The method of above was repeated using the following components:

| Ingredient | mg/dose | % |
|---|---|---|
| Flucytosine (5-FC) | 500 | 58.82% |
| Carbopol (71G) | 150 | 17.65% |
| Nusiline US2 | 100 | 11.76% |
| Lubritab | 100 | 11.76% |
| Total | 850 | 100.0% |

Example 7

The method of above was repeated using the following components:

| Ingredient | mg/dose | % |
|---|---|---|
| Flucytosine (5-FC) | 500 | 56.82% |
| Carbopol (71G) | 120 | 13.64% |
| HPC (Klucel-H) | 50 | 5.68% |
| Lactose | 200 | 22.73% |
| Mg Stearate | 10 | 1.14% |
| Total | 880 | 100.0% |

Example 8

The method of above was repeated using the following components:

| Ingredient | mg/tab | w/w % |
|---|---|---|
| 5-Flurocytosine | 500 | 44.6 |
| Carbopol ® 71G NF | 175 | 15.6 |
| HPC (Klucel ® EXF) | 67 | 6.0 |
| Lactose | 120 | 10.7 |
| Dicalcium Phosphate (Emcompress ®) NF | 250 | 22.3 |
| Magnesium Stearate NF | 10 | 0.9 |
| Total | 1122 | 100.0 |

Example 9

The method of above was repeated using the following components:

| Material | mg/tab | w/w % |
|---|---|---|
| 5-Flurocytosine | 500 | 44.6 |
| Kollidon ® SR | 175 | 15.6 |
| HPC (Klucel ® EXF) | 67 | 6.0 |
| Lactose | 120 | 10.7 |
| Dicalcium Phosphate (Emcompress ®) NF | 250 | 22.3 |
| Magnesium Stearate NF | 10 | 0.9 |
| Total | 1122 | 100.0 |

Example 10

The method of above was repeated using the following components:

| Material | mg/tab | w/w % |
|---|---|---|
| 5-Flurocytosine | 500 | 44.6 |
| HPC (Klucel ® HXF) | 175 | 15.6 |
| HPC (Klucel ® EXF) | 67 | 6.0 |
| Lactose | 120 | 10.7 |
| Dicalcium Phosphate (Emcompress ®) NF | 250 | 22.3 |
| Magnesium Stearate NF | 10 | 0.9 |
| Total | 1122 | 100.0 |

Example 11

The method of above was repeated using the following components:

| Material | mg/tab | w/w % |
|---|---|---|
| 5-Flurocytosine | 500 | 44.6 |
| Methocel ® K100M | 175 | 15.6 |
| HPC (Klucel ® EXF) | 67 | 6.0 |
| Lactose | 120 | 10.7 |
| Dicalcium Phosphate (Emcompress ®) NF | 250 | 22.3 |
| Magnesium Stearate NF | 10 | 0.9 |
| Total | 1122 | 100.0 |

Example 12

The method of above was repeated using the following components:

| Material | mg/tab | w/w % |
|---|---|---|
| 5-Flurocytosine | 500 | 54.7 |
| Eudragit ® RLPO | 100 | 10.9 |
| Ethocel ® 10 cp | 100 | 10.9 |
| HPC (Klucel ® EXF) | 55 | 6.0 |
| Lactose | 50 | 5.5 |
| Dicalcium Phosphate (Emcompress ®) NF | 100 | 10.9 |
| Magnesium Stearate NF | 9 | 1.0 |
| Total | 1122 | 100.0 |

Example 13

The method of above was repeated using the following components:

| Material | mg/tab | w/w % |
|---|---|---|
| 5-Flurocytosine | 500 | 44.1 |
| Kollidon ® SR | 185 | 16.3 |
| HPC (Klucel ® EXF) | 68 | 6.0 |
| Maltodextrin | 120 | 10.6 |
| Dicalcium Phosphate (Emcompress ®) NF | 250 | 22.1 |
| Magnesium Stearate NF | 10 | 0.9 |
| Total | 1133 | 100.0 |

Example 14

The method of above was repeated using the following components:

| Material | mg/tab | w/w % |
|---|---|---|
| 5-Flurocytosine | 500 | 50.1 |
| Carbopol ® 71G NF | 110 | 11.0 |
| HPC (Klucel ® EXF) | 60 | 6.0 |
| Maltodextrin M510 | 180 | 18.0 |
| Dicalcium Phosphate (Emcompress ®) NF | 140 | 14.0 |
| Magnesium Stearate NF | 9 | 0.9 |
| Total | 999 | 100 |

Example 15

The method of above was repeated using the following components:

| Material | mg/tab | w/w % |
|---|---|---|
| 5-Flurocytosine | 500 | 50.1 |
| Carbopol ® 71G NF | 110 | 11.0 |
| HPC (Klucel ® EXF) | 60 | 6.0 |
| Microcrystalline Cellulose (Avicel ® PH102) | 180 | 18.0 |
| Dicalcium Phosphate (Emcompress ®) NF | 140 | 14.0 |
| Magnesium Stearate NF | 9 | 0.9 |
| Total | 999 | 100.0 |

Example 16

The method of above was repeated using the following components:

| Material | mg/tab | w/w % |
|---|---|---|
| 5-Flurocytosine | 500 | 49.6 |
| Methocel ® K100M | 80 | 7.9 |
| HPC (Klucel ® EXF) | 60 | 5.9 |
| Maltodextrin M510 | 200 | 19.8 |
| Dicalcium Phosphate (Emcompress ®) NF | 160 | 15.9 |
| Magnesium Stearate NF | 9 | 0.9 |
| Total | 1009 | 100.0 |

Example 17

The method of above was repeated using the following components:

| Material | mg/tab | w/w % |
|---|---|---|
| 5-Flurocytosine | 500 | 49.6 |
| Methocel ® K100M | 80 | 7.9 |
| HPC (Klucel ® EXF) | 60 | 5.9 |
| Microcrystalline Cellulose (Avicel ® PH102) | 200 | 19.8 |
| Dicalcium Phosphate (Emcompress ®) NF | 160 | 15.9 |
| Magnesium Stearate NF | 9 | 0.9 |
| Total | 1009 | 100.0 |

Example 18

The method of above was repeated using the following components:

| Material | mg/tab | w/w % |
|---|---|---|
| 5-Flurocytosine | 500 | 50.1 |
| Eudragit ® RLPO | 77 | 7.7 |
| Ethocel ® 100 cp* | 77 | 7.7 |
| HPC (Klucel ® EXF) | 60 | 6.0 |
| Maltodextrin M510 | 138 | 13.8 |
| Dicalcium Phosphate (Emcompress ®) NF | 138 | 13.8 |
| Magnesium Stearate NF | 9 | 0.9 |
| Total | 999 | 100.0 |

Example 19

The method of above was repeated using the following components:

| Material | mg/tab | w/w % |
|---|---|---|
| 5-Flurocytosine | 500 | 55.31 |
| Carbopol-71G | 110 | 12.17 |
| HPC (Klucel EXF) | 55 | 6.08 |
| Microcrystalline Cellulose (Avicel PH102) | 100 | 11.06 |
| Dicalcium Phosphate Dihydrate | 130 | 14.38 |
| Magneisum Stearate (Veg Derived) | 9 | 1.00 |
| Core tablet-total | 904 | 100.00 |

Carbopol tablets-uncoated were used in dog studies.
Carbopol-coated tablets were used in human studies.

Example 20

The tablets of Example 1-19 may be coated with immediate release HPMC based coating material such as Opadry (Colorcon) for esthetic purpose. An example of coated tablets of core tablets prepared in Example 19 is shown here.

| Ingredient | mg/tab | % w/w |
|---|---|---|
| Core tablet | 904 | 97.1 |
| Opadry II Clear YS-1-7006 | 27.1 | 2.9 |
| Purified Water | * | * |
| Total Coated Tablet | 931 | 100 |

The tablets of Example 20 were used in a single dose human PK study and also shown as "Carbopol" formulation.

Example 21

The coated tablets of core tablets prepared in Example 13 are shown here.

| Ingredient | mg/tab | % w/w |
|---|---|---|
| Core tablet | 1133 | 97.1 |
| Opadry II Clear YS-1-7006 | 34 | 2.9 |
| Purified Water | * | * |
| Total Coated Tablet | 1167 | 100 |

The tablets of Example 21 were used in a single dose human PK study and also shown as "Kollidon" formulation.

Example 22

Flucytosine USP Dissolution Test

For the measurement of release rate in-vitro, the dissolution method for Ancobon® described in USP 31 was used with only a small modification. All data reported in this report is average rate of dissolution at a specific time point (n=4 or 8).

In-vitro dissolution measurement parameters used in evaluating in-vitro drug release rate in new dosage forms are shown in Table A.

TABLE A

Dissolution Method Used in Formulation Development

| VK 7000 Dissolution Apparatus | Specification |
|---|---|
| Apparatus | USP apparatus II (Paddle) |
| Temperature | 37° C. |
| RPM | 75 rpm |
| Vessels | One liter capacity |
| Dissolution Medium | 900 ml of deionized water |
| Sampling | Manual |
| Sampling Volume | 10.0 ml |
| Sample Interval | T = 0.5 h, 1 h, 1.5 h, 3 h, 5 h, 7 h, 9 h, 11 h, and 12 h |
| Volume Replacement | No volume replacement |
| Sample Filtration | 0.45 µm PVDF Filter |
| Sample analysis | UV-Vis spectrophotometer at 275 nm |

The results of the average dissolution rate (% drug released) using the method described above are shown in Table B and the compilation of the dissolution curves are shown in FIG. 1.

TABLE B

Average Dissolution Rate of First twelve Prototypes

| Time (Hr) | Example 8 Carbopol | Example 9 Kollidon | Example 10 HPC | Example 11 HPMC | Example 12 Eudragit/EC |
|---|---|---|---|---|---|
| 0 | 0 | 0 | 0 | 0 | 0 |
| 0.5 | 8 | 31 | 9 | 10 | 17 |
| 1 | 11 | 43 | 13 | 15 | 29 |
| 1.5 | 16 | 52 | 16 | 19 | 44 |
| 2 | 19 | 59 | 20 | 22 | 53 |
| 3 | 26 | 71 | 26 | 28 | 71 |
| 5 | 40 | 87 | 35 | 38 | 92 |
| 7 | 52 | 98 | 43 | 48 | 103 |
| 8 | 58 | 100 | 47 | 53 | 104 |
| 10 | 68 | 104 | 53 | 61 | 106 |

| Time | Example 18 Eud/EU/Maltrin | Example 13 Kollidon/Maltrin | Example 14 Carbopol/Maltrin | Example 16 HPMC/Maltrin | Example 17 HPMC/MCC | Example 15 Carbopol/MCC |
|---|---|---|---|---|---|---|
| 0 | 0 | 0 | 0 | 0 | 0 | 0 |
| 0.5 | 23 | 23 | 7 | 15 | 23 | 7 |
| 1.5 | 49 | 39 | 17 | 26 | 34 | 14 |
| 3 | 75 | 55 | 28 | 39 | 46 | 24 |
| 5 | 91 | 69 | 43 | 53 | 57 | 38 |
| 7 | 99 | 78 | 56 | 65 | 67 | 52 |
| 9 | 103 | 86 | 75 | 76 | 75 | 84 |
| 11 | 102 | 92 | 75 | 91 | 82 | 102 |

| Time | Example 19 Carbopol/MCC |
|---|---|
| 0 | 0 |
| 0.5 | 7 |
| 1.5 | 14 |
| 3 | 25 |
| 5 | 38 |
| 7 | 52 |
| 9 | 90 |
| 11 | 101 |

The dissolution results showed that all formulations showed extended release profiles of 5-FC over time.

Example 23

Swelling and Erosion Rate Test Method.

The gastric retention of a matrix tablet relies on the tablet to swell quickly by absorbing gastric fluid upon ingestion while having an acceptable mechanical strength over time so as not to break up into small pieces in the stomach. The rate of medium uptake into the tablet (i.e., swelling rate) and tablet erosion rate (i.e., measure of mechanical strength) were determined after immersion in the pH 4.1 SGF medium, which simulates the pH of the fed stomach. Weighted samples were placed in dissolution vessels (USP type I or II dissolution apparatus) containing pH 4.1 buffer at 37±0.2° C. After a selected time interval (e.g., 1 h, 2 h, 3 h, 5 h, 8 h, 12 h, and 24 h) each dissolution basket was withdrawn, blotted to remove excess water from the tablets, and the dimension (length and width) were measured in triplicate. The tablets were then weighed (within 10 minutes of the withdrawal from the medium so as prevent from drying) on an analytical balance. The wetted samples were then dried in an oven at >100° C. for at least 24 hours, allowed to cool in a desiccator, and finally weighed until constant weight was achieved (final dry weight). The increase in weight of the wet mass represents the medium uptake. The increase in weight due to absorbed liquid (Q) was estimated according equation 1.

$$Q = 100(W_W - W_f)/W_f \quad \text{Equation 1}$$

Where $W_W$ and $W_f$ are the mass of the hydrated sample before drying and final mass of the same dried and partially eroded sample, respectively.

The percentage erosion (E) of the device was estimated using equation 2.

$$E = 100(W_I - W_f)/W_I \quad \text{Equation 2}$$

Where $W_I$ is the initial starting dry weight. Three different samples were measured for each time point, and fresh samples were used for each individual time point. All experiments were done in triplicate using three tablets of each comparator drug.

Based on the dissolution profile, the compositions of Example 18 (Eudragit/EC prototype with Maltodextrin), Example 13 (Kollidon), and Example 19 (Carbopol prototypes) were selected for further study. The quicker the tablets swell upon ingestion, the better probability the matrix tablet will be retained in the upper GI track. Of the three prototypes, Carbopol prototype swelled quicker than the other two by absorbing about 50% of its dry weight in water in 30 minutes, and continues to absorb the water to almost 250% of its dry weight in 8 hours. Kollidon and Eudragit prototypes behaved very similar in that both absorbed water very slowly over time to about 50% of its dry weight in eight hours. From these results, Carbopol tablets are the swelling type matrix while the other two prototypes did not swell much. The rate of erosion for these three prototypes was Carbopol>Kollidon≈Eudragit prototype formulation.

Since the tablet size is a factor for retention in the stomach, a slower erosion rate is preferred for this type of formulation. The erosion rate of tablets under the dissolution conditions (USP I, basket) is expressed by the E ratio (% of tablet weight loss, dry weight).

The data showed that Carbopol prototype was the slowest to erode over 8 hours (loss of ~30% tablet weight in 8 hours) under the USP I dissolution conditions while the other two prototypes eroded quicker. The rate of erosion for these three prototypes was Carbopol<Kollidon<Eudragit prototype formulation.

A HPMC tablet also could serve as a slow-release matrix tablet for 5-FC, but Carbopol has the added benefit of being a bioadhesive tablet. Smaller tablets gives an advantage of easier swallowability while providing enough retention time in the upper GI.

Example 24

Dissolution at various pH conditions—All dissolution testing for ranking of various prototypes in formulation development rounds was performed using deionized water as the dissolution medium as described in Ancobon's USP monograph. In order to test if there is any changes in dissolution profile of Flucytosine-XR tablet prototypes, the three final candidates were tested for dissolution in two different pH conditions—at pH 1.2 (SGF) and pH 4.1 (USP acetate buffer). The results are listed in Table C and show the dissolution profiles of the three prototypes at various pH conditions.

TABLE C

Average dissolution rate of three recommended formulation at various pHs

| Time hour | Ex 18 Eud/EU/Matrin | | | Ex 13 Kollidon/Maltrin | | | Ex 19 Carbopol/MCC | | |
|---|---|---|---|---|---|---|---|---|---|
| | pH 7 | pH 4.1 | pH 1.2 | pH 7 | pH 4.1 | pH 1.2 | pH 7 | pH 4.1 | pH 1.2 |
| 0 | 0 | 0 | 0 | 0 | 0 | 0 | 0 | 0 | 0 |
| 0.5 | 23 | 24 | 33 | 23 | 22 | 28 | 7 | 8 | 12 |
| 1.5 | 49 | 55 | 74 | 39 | 45 | 52 | 14 | 15 | 23 |
| 3 | 75 | 87 | 102 | 55 | 63 | 71 | 25 | 25 | 41 |
| 5 | 91 | 101 | 103 | 69 | 78 | 84 | 38 | 39 | 66 |
| 7 | 99 | 102 | 103 | 78 | 87 | 93 | 52 | 53 | 85 |
| 9 | 103 | 103 | 105 | 86 | 93 | 97 | 90 | 88 | 98 |
| 11 | 102 | 103 | 105 | 92 | 98 | 101 | 101 | 102 | 104 |

The effect of pH in the dissolution profile of the three prototypes was slightly different, but in general the drug release rate increased in more acidic media. The individual matrix tablet's behavior is summarized below:

Example 18 (Eudragit/Ethocel based tablet): The pH effect was greatest in this prototype. As the pH is decreased the drug release rate increased from a 7 hour (>95% release) at pH 7 to 5 hour at pH 4.1 to 3 hours at pH 1.2. This is unusual considering the matrix tablet components are purported to be insensitive to pH ranges.

Example 13 (Kollidon-based matrix tablets): Full release of the drug increased slightly when the pH of the dissolution media was changed from pH 7 to pH 4.1, and then to pH 1.2. Complete release of drug was achieved at about 9 hours in pH 1.2 while it took >11 hours in pH 7.

Example 19 (Carbopol-based matrix tablets): the dissolution profile remained the same at pH 7 and pH 4.1 in virtual overlap for the whole profile. At pH 1.2, the release rate was slightly faster and it had a more linear release rate than at either pH 4.1 or at pH 7.

Example 25

A clinical trial was performed to determine the properties of the two formulations, Example 20 (coated Carbopol) and Example 21 (coated Kollidon) compared to Ancobon® (reference formulation) in humans, as described below. Formulation A is Carbopol with formulation shown in Example 20, formulation B is Kollidon with formulation shown in Example 21.

| | |
|---|---|
| Title | A Pilot Study to Assess the Single-Dose Pharmacokinetics of Two Test Formulations of Flucytosine Under Fed and Fasting Conditions |
| Study Objective | The objective of this study assessed the single-dose bioavailability of two test extended-release formulations of flucytosine 500 mg tablets under fasting and fed conditions compared to Ancobon ® 500 mg immediate-release flucytosine capsules under fasted conditions. Safety was monitored. |
| Study Design | Open-label, randomized, 5-way crossover study. |
| Number of Subjects | 8 subjects were enrolled in the study. |
| Duration of Participation for Subjects | The duration of participation for each subject was approximately 11 days, not including the Screening Period. Subjects were confined beginning on Day −1 through completion of procedures on the morning of Day 10. |
| Study Products | Test Formulation A (Carbopol): 500 mg flucytosine extended-release tablets for oral administration<br>Test Formulation B (Kollidon): 500 mg flucytosine extended-release tablets for oral administration<br>Reference Formulation: 500 mg flucytosine immediate-release capsules (Ancobon ®, Valeant Pharmaceuticals) for oral administration |
| Study Treatments | Treatment A = Test Formulation A fasted<br>Treatment B = Test Formulation A fed<br>Treatment C = Test Formulation B fasted<br>Treatment D = Test Formulation B fed<br>Treatment E = Reference Product fasted |
| Pharmacokinetic Sample Collection and Analysis | Serial blood samples were collected pre-dose and at 1, 3, 4, 5, 6, 9, 12, 18 and 24 hours post-dose during Treatments A, B, C, and D and pre-dose and at 0.5, 1, 2, 3, 4, 6, 8, 10, and 12 hours post-dose during Treatment E to determine concentration of flucytosine and fluorouracil in plasma. Standard noncompartmental pharmacokinetic (PK) parameters, including $AUC_{0-t}$, $AUC_{0-inf}$, $AUC_{0-t}/AUC_{0-inf}$, $C_{max}$, $t_{max}$, $k_{el}$, and $t_{1/2}$, were calculated from the individual plasma concentrations of flucytosine and fluorouracil. Comparisons of selected PK parameters and the fluorouracil AUC to flucytosine AUC ratio were made among the treatments. Modeling was performed to explore how the test formulations is dosed clinically (i.e., number of daily doses) to achieve flucytosine steady-state concentrations between 40 and 100 µg/mL. |
| Safety Assessments | Physical examinations, body height and weight, vital signs, clinical laboratory profiles, and adverse events (AEs) were assessed at designated time points. |

"Fasting" Treatments include subjects that were required to fast (defined as no caloric intake) for a minimum of 10 hours overnight prior to study drug administration and continue to fast for at least 4 hours thereafter. Water (except that administered with dosing) was not permitted from 1 hour before until 1 hour after dosing. Water was allowed as desired at all other times and adequate hydration was encouraged. Standard meals were provided uniformly approximately 4 and 9 hours after dosing, and an evening snack was provided approximately 12-13 hours after dosing.

"Fed" Treatments included subjects that were required to fast overnight for at least 10 hours. Thirty (30) minutes prior to their scheduled dosing times they were given a standard high-fat breakfast which was substantially or completely consumed within 30 minutes. The breakfast consisted of 2 slices of buttered toast, 2 fried eggs, 2 strips of bacon, 1 serving of hash brown potatoes, and 240 mL of whole milk. Subjects were asked to fast for at least 4 hours following dosing. Water (except that administered with dosing) was not permitted from 1 hour before until 1 hour after dosing. Water was allowed as desired at all other times and adequate hydration was encouraged. Standard meals were provided uniformly approximately 4 and 9 hours after dosing, and an evening snack was provided approximately 12-13 hours after dosing.

Blood was drawn into (5 mL) chilled evacuated tubes containing $K_3$ EDTA and stored in an ice bath until centrifuged (~2500 rpm at 4° C. for 10 minutes). After centrifuging, two aliquots of plasma (the first containing at least 1 mL and the second containing the remainder) were removed and placed in appropriately labeled polypropylene vials. Within 60 minutes of sample collection, the aliquots were stored in a freezer set at −20° C.±10° C. or below until shipped for analysis to a contractor.

5-Fluorocytosine was quantified from the human plasma by extracting an aliquot of sample against known standard calibrators. After adding a stable isotope labeled internal standard, the samples were processed with protein-precipitation in acetonitrile. A portion of the supernatant was removed and sealed in a 96-well plate. Samples were analyzed via LC-MS/MS utilizing Hydrophilic Interaction Liquid Chromatography (HILIC) in tandem with an AB|MDS Sciex API 4000 triple quadrupole mass spectrometer using an APCI source. Negative ions were monitored in the multiple reaction monitoring (MRM) mode. Results are summarized in Table D (based upon tables $D_{sub1-5}$).

TABLE D

5-FC ER Formulations vs Ancobon - Single Dose PK Parameters

|  | Ancobon fasted | Carbopol fasted | Carbopol fed | Kollidon fasted | Kollidon fed |
|---|---|---|---|---|---|
| Cmax (µg/ml) | 7.30 | 2.56 | 6.14 | 1.98 | 3.63 |
| CV | 10 | 29 | 28 | 22 | 15 |
| Tmax (h) | 1.63 | 3.88 | 5.62 | 3.58 | 7.86 |
| CV | 0.5 | 17 | 31 | 22 | 34 |
| AUC (0-inf) µg · h/ml | 57.3 | 28.1 | 54.3 | 20.8 | 47.7 |
| CV | 4 | 28 | 14 | 26 | 25 |
| T½ (h) | 4.80 | 6.55 | 5.61 | 5.93 | 5.55 |
| CV | 15 | 30 | 23 | 22 | 18 |

TABLE $D_{sub1}$

Plasma Flucytosine Pharmacokinetic Parameters Following Administration of 1 × 500 mg Flucytosine ER Tablet (Test Formulation A) PO under Fasted Conditions (Treatment A)

| Subject Number | Treatment Sequence | Study Period | Parameters | | | | |
|---|---|---|---|---|---|---|---|
| | | | Cmax µg/mL | tmax hr | AUC(0-t) µg * hr/mL | AUC(0-inf) µg * hr/mL | t½ hr |
| 1 | DECAB | 4 | 2.59 | 3.00 | 24.7 | 30.7 | 7.12 |
| 2 | BCADE | 3 | 2.11 | 4.00 | 13.4 | 17.8 | 5.16 |
| 3 | CDBEA | 5 | 2.04 | 4.00 | 25.4 | 33.1 | 10.7 |
| 4 | ABECD | 1 | 2.66 | 4.00 | 24.8 | 31.4 | 7.49 |
| 5 | CDBEA | 5 | 4.07 | 5.00 | 34.1 | 37.9 | 4.75 |
| 6 | DECAB | 4 | 2.27 | 4.00 | 16.7 | 25.2 | 6.57 |
| 7 | ABE___ | 1 | 3.07 | 4.00 | 28.5 | 33.0 | 5.84 |
| 8 | BCADE | 3 | 1.68 | 3.00 | 10.6 | 15.8 | 4.71 |
| Mean | | | 2.56 | 3.88 | 22.3 | 28.1 | 6.55 |
| SD | | | 0.745 | 0.642 | 7.99 | 7.83 | 1.99 |
| CV (%) | | | 29.1 | 16.6 | 35.9 | 27.9 | 30.5 |
| SEM | | | 0.263 | 0.227 | 2.83 | 2.77 | 0.705 |
| N | | | 8.00 | 8.00 | 8.00 | 8.00 | 8.00 |
| Median | | | 2.43 | 4.00 | 24.8 | 31.0 | 6.21 |
| Minimum | | | 1.68 | 3.00 | 10.6 | 15.8 | 4.71 |
| Maximum | | | 4.07 | 5.00 | 34.1 | 37.9 | 10.7 |
| Geom. Mean | | | 2.48 | — | 20.9 | 27.0 | — |

| Subject | Parameters | | | | |
|---|---|---|---|---|---|
| | Kel | | | ln-Parameters | |
| Number | 1/hr | AUCR | ln(Cmax) | ln[AUC(0-t)] | ln[AUC(0-inf)] |
| 1 | 0.0973 | 0.805 | 0.952 | 3.21 | 3.42 |
| 2 | 0.134 | 0.754 | 0.747 | 2.60 | 2.88 |
| 3 | 0.0645 | 0.765 | 0.713 | 3.23 | 3.50 |
| 4 | 0.0925 | 0.792 | 0.978 | 3.21 | 3.45 |
| 5 | 0.146 | 0.900 | 1.40 | 3.53 | 3.64 |
| 6 | 0.106 | 0.664 | 0.820 | 2.82 | 3.23 |
| 7 | 0.119 | 0.865 | 1.12 | 3.35 | 3.50 |

TABLE D$_{sub1}$-continued

Plasma Flucytosine Pharmacokinetic Parameters Following
Administration of 1 × 500 mg Flucytosine ER Tablet (Test Formulation A)
PO under Fasted Conditions (Treatment A)

|  |  |  |  |  |  |
|---|---|---|---|---|---|
| 8 | 0.147 | 0.671 | 0.519 | 2.36 | 2.76 |
| Mean | 0.113 | 0.777 | 0.907 | 3.04 | 3.30 |
| SD | 0.0288 | 0.0831 | 0.273 | 0.403 | 0.317 |
| CV (%) | 25.5 | 10.7 | 30.1 | 13.3 | 9.61 |
| SEM | 0.0102 | 0.0294 | 0.0965 | 0.143 | 0.112 |
| N | 8.00 | 8.00 | 8.00 | 8.00 | 8.00 |
| Median | 0.112 | 0.779 | 0.886 | 3.21 | 3.43 |
| Minimum | 0.0645 | 0.664 | 0.519 | 2.36 | 2.76 |
| Maximum | 0.147 | 0.900 | 1.40 | 3.53 | 3.64 |
| Geom. Mean | — | — | — | — | — |

— = Value missing or not reportable.

TABLE D$_{sub2}$

Plasma Flucytosine Pharmacokinetic Parameters Following
Administration of 1 × 500 mg Flucytosine ER Tablet (Test Formulation A)
PO under Fed Conditions (Treatment B)

| Subject Number | Treatment Sequence | Study Period | Parameters | | | | |
|---|---|---|---|---|---|---|---|
| | | | Cmax µg/mL | tmax hr | AUC(0-t) µg * hr/mL | AUC(0-inf) µg * hr/mL | t½ hr |
| 1 | DECAB | 5 | 9.35 | 5.00 | 51.4 | 57.9 | 4.60 |
| 2 | BCADE | 1 | 4.97 | 6.00 | 47.6 | 52.4 | 6.10 |
| 3 | CDBEA | 3 | 6.94 | 6.00 | 53.9 | 58.2 | 5.45 |
| 4 | ABECD | 2 | 6.33 | 9.00 | 59.4 | 62.9 | 4.53 |
| 5 | CDBEA | 3 | 6.80 | 4.00 | 49.9 | 55.8 | 5.25 |
| 6 | DECAB | 5 | 5.62 | 6.00 | 51.0 | 55.8 | 5.88 |
| 7 | ABE___ | 2 | 5.88 | 6.00 | 48.0 | 54.9 | 4.68 |
| 8 | BCADE | 1 | 3.26 | 3.00 | 29.2 | 36.9 | 8.39 |
| Mean | | | 6.14 | 5.62 | 48.8 | 54.3 | 5.61 |
| SD | | | 1.75 | 1.77 | 8.75 | 7.67 | 1.27 |
| CV (%) | | | 28.5 | 31.4 | 17.9 | 14.1 | 22.6 |
| SEM | | | 0.618 | 0.625 | 3.09 | 2.71 | 0.448 |
| N | | | 8.00 | 8.00 | 8.00 | 8.00 | 8.00 |
| Median | | | 6.11 | 6.00 | 50.4 | 55.8 | 5.35 |
| Minimum | | | 3.26 | 3.00 | 29.2 | 36.9 | 4.53 |
| Maximum | | | 9.35 | 9.00 | 59.4 | 62.9 | 8.39 |
| Geom. Mean | | | 5.91 | — | 47.9 | 53.8 | — |

| Subject Number | Parameters | | | | |
|---|---|---|---|---|---|
| | Kel 1/hr | AUCR | ln-Parameters | | |
| | | | ln(Cmax) | ln[AUC(0-t)] | ln[AUC(0-inf)] |
| 1 | 0.151 | 0.887 | 2.24 | 3.94 | 4.06 |
| 2 | 0.114 | 0.909 | 1.60 | 3.86 | 3.96 |
| 3 | 0.127 | 0.927 | 1.94 | 3.99 | 4.06 |
| 4 | 0.153 | 0.944 | 1.85 | 4.08 | 4.14 |
| 5 | 0.132 | 0.894 | 1.92 | 3.91 | 4.02 |
| 6 | 0.118 | 0.915 | 1.73 | 3.93 | 4.02 |
| 7 | 0.148 | 0.874 | 1.77 | 3.87 | 4.00 |
| 8 | 0.0826 | 0.791 | 1.18 | 3.37 | 3.61 |
| Mean | 0.128 | 0.892 | 1.78 | 3.87 | 3.99 |
| SD | 0.0237 | 0.0466 | 0.304 | 0.212 | 0.161 |
| CV (%) | 18.5 | 5.23 | 17.1 | 5.48 | 4.03 |
| SEM | 0.00837 | 0.0165 | 0.107 | 0.0750 | 0.0568 |
| N | 8.00 | 8.00 | 8.00 | 8.00 | 8.00 |
| Median | 0.130 | 0.901 | 1.81 | 3.92 | 4.02 |
| Minimum | 0.0826 | 0.791 | 1.18 | 3.37 | 3.61 |
| Maximum | 0.153 | 0.944 | 2.24 | 4.08 | 4.14 |
| Geom. Mean | — | — | — | — | — |

— = Value missing or not reportable.

TABLE D$_{sub3}$

Plasma Flucytosine Pharmacokinetic Parameters Following
Administration of 1 × 500 mg Flucytosine ER Tablet (Test Formulation B)
PO under Fasted Conditions (Treatment C)

| Subject Number | Treatment Sequence | Study Period | Parameters | | | | |
|---|---|---|---|---|---|---|---|
| | | | Cmax μg/mL | tmax hr | AUC(0-t) μg*hr/mL | AUC(0-inf) μg*hr/mL | t½ hr |
| 1 | DECAB | 3 | 2.23 | 3.05 | 12.2 | 19.1 | 5.36 |
| 2 | BCADE | 2 | 1.98 | 3.00 | 12.2 | 18.2 | 4.79 |
| 3 | CDBEA | 1 | 1.99 | 3.00 | 20.2 | 25.3 | 7.01 |
| 4 | ABECD | 4 | 2.70 | 4.00 | 25.1 | 30.7 | 7.27 |
| 5 | CDBEA | 1 | 2.06 | 5.00 | 15.6 | 19.2 | 3.99 |
| 6 | DECAB | 3 | 1.60 | 4.00 | 12.7 | 17.9 | 5.97 |
| 8 | BCADE | 2 | 1.33 | 3.00 | 8.33 | 15.1 | 7.14 |
| Mean | | | 1.98 | 3.58 | 15.2 | 20.8 | 5.93 |
| SD | | | 0.439 | 0.780 | 5.69 | 5.35 | 1.28 |
| CV (%) | | | 22.1 | 21.8 | 37.5 | 25.7 | 21.6 |
| SEM | | | 0.166 | 0.295 | 2.15 | 2.02 | 0.484 |
| N | | | 7.00 | 7.00 | 7.00 | 7.00 | 7.00 |
| Median | | | 1.99 | 3.05 | 12.7 | 19.1 | 5.97 |
| Minimum | | | 1.33 | 3.00 | 8.33 | 15.1 | 3.99 |
| Maximum | | | 2.70 | 5.00 | 25.1 | 30.7 | 7.27 |
| Geom. Mean | | | 1.94 | — | 14.3 | 20.3 | — |

| Subject Number | Parameters | | | | |
|---|---|---|---|---|---|
| | Kel 1/hr | AUCR | ln-Parameters | | |
| | | | ln(Cmax) | ln[AUC(0-t)] | ln[AUC(0-inf)] |
| 1 | 0.129 | 0.638 | 0.802 | 2.50 | 2.95 |
| 2 | 0.145 | 0.672 | 0.683 | 2.50 | 2.90 |
| 3 | 0.0988 | 0.797 | 0.688 | 3.01 | 3.23 |
| 4 | 0.0954 | 0.817 | 0.993 | 3.22 | 3.43 |
| 5 | 0.174 | 0.815 | 0.723 | 2.75 | 2.95 |
| 6 | 0.116 | 0.710 | 0.470 | 2.54 | 2.89 |
| 8 | 0.0971 | 0.550 | 0.285 | 2.12 | 2.72 |
| Mean | 0.122 | 0.714 | 0.663 | 2.66 | 3.01 |
| SD | 0.0293 | 0.102 | 0.228 | 0.365 | 0.239 |
| CV (%) | 24.0 | 14.3 | 34.4 | 13.7 | 7.93 |
| SEM | 0.0111 | 0.0385 | 0.0863 | 0.138 | 0.0902 |
| N | 7.00 | 7.00 | 7.00 | 7.00 | 7.00 |
| Median | 0.116 | 0.710 | 0.688 | 2.54 | 2.95 |
| Minimum | 0.0954 | 0.550 | 0.285 | 2.12 | 2.72 |
| Maximum | 0.174 | 0.817 | 0.993 | 3.22 | 3.43 |
| Geom. Mean | — | — | — | — | — |

— = Value missing or not reportable.

TABLE D$_{sub4}$

Plasma Flucytosine Pharmacokinetic Parameters Following
Administration of 1 × 500 mg Flucytosine ER Tablet (Test Formulation B)
PO under Fed Conditions (Treatment D)

| Subject Number | Treatment Sequence | Study Period | Parameters | | | | |
|---|---|---|---|---|---|---|---|
| | | | Cmax μg/mL | tmax hr | AUC(0-t) μg*hr/mL | AUC(0-inf) μg*hr/mL | t½ hr |
| 1 | DECAB | 1 | 3.30 | 4.00 | 36.2 | 41.9 | 4.66 |
| 2 | BCADE | 4 | 3.93 | 12.0 | 56.0 | — | — |
| 3 | CDBEA | 2 | 3.65 | 9.00 | 48.0 | 54.0 | 5.89 |
| 4 | ABECD | 5 | 4.32 | 9.00 | 56.3 | 62.0 | 5.17 |
| 5 | CDBEA | 2 | 4.20 | 6.00 | 35.7 | 41.5 | 5.15 |
| 6 | DECAB | 1 | 3.15 | 9.00 | 46.7 | 56.5 | 7.47 |
| 8 | BCADE | 4 | 2.85 | 6.00 | 26.4 | 30.2 | 4.96 |
| Mean | | | 3.63 | 7.86 | 43.6 | 47.7 | 5.55 |
| SD | | | 0.554 | 2.68 | 11.2 | 11.8 | 1.02 |
| CV (%) | | | 15.3 | 34.1 | 25.7 | 24.8 | 18.4 |
| SEM | | | 0.209 | 1.01 | 4.24 | 4.83 | 0.418 |
| N | | | 7.00 | 7.00 | 7.00 | 6.00 | 6.00 |
| Median | | | 3.65 | 9.00 | 46.7 | 48.0 | 5.16 |
| Minimum | | | 2.85 | 4.00 | 26.4 | 30.2 | 4.66 |

TABLE D$_{sub4}$-continued

Plasma Flucytosine Pharmacokinetic Parameters Following
Administration of 1 × 500 mg Flucytosine ER Tablet (Test Formulation B)
PO under Fed Conditions (Treatment D)

| | | | | | |
|---|---|---|---|---|---|
| Maximum | | 4.32 | 12.0 | 56.3 | 62.0 | 7.47 |
| Geom. Mean | | 3.59 | — | 42.3 | 46.4 | — |

| | Parameters | | | | |
|---|---|---|---|---|---|
| Subject | Kel | | ln-Parameters | | |
| Number | 1/hr | AUCR | ln(Cmax) | ln[AUC(0-t)] | ln[AUC(0-inf)] |
| 1 | 0.149 | 0.865 | 1.19 | 3.59 | 3.74 |
| 2 | — | — | 1.37 | 4.03 | — |
| 3 | 0.118 | 0.888 | 1.29 | 3.87 | 3.99 |
| 4 | 0.134 | 0.908 | 1.46 | 4.03 | 4.13 |
| 5 | 0.135 | 0.861 | 1.44 | 3.58 | 3.73 |
| 6 | 0.0928 | 0.827 | 1.15 | 3.84 | 4.03 |
| 8 | 0.140 | 0.876 | 1.05 | 3.27 | 3.41 |
| Mean | 0.128 | 0.871 | 1.28 | 3.74 | 3.84 |
| SD | 0.0199 | 0.0275 | 0.155 | 0.277 | 0.266 |
| CV (%) | 15.6 | 3.15 | 12.2 | 7.39 | 6.93 |
| SEM | 0.00814 | 0.0112 | 0.0587 | 0.105 | 0.109 |
| N | 6.00 | 6.00 | 7.00 | 7.00 | 6.00 |
| Median | 0.134 | 0.870 | 1.29 | 3.84 | 3.86 |
| Minimum | 0.0928 | 0.827 | 1.05 | 3.27 | 3.41 |
| Maximum | 0.149 | 0.908 | 1.46 | 4.03 | 4.13 |
| Geom. Mean | — | — | — | — | — |

— = Value missing or not reportable.

TABLE D$_{sub5}$

Plasma Flucytosine Pharmacokinetic Parameters Following Administration
of 1 × 500 mg Flucytosine IR Capsule (Reference Formulation - Ancobon,
Valeant Pharmaceuticals) PO under Fasted Conditions (Treatment E)

| | | | Parameters | | | | |
|---|---|---|---|---|---|---|---|
| Subject Number | Treatment Sequence | Study Period | Cmax µg/mL | tmax hr | AUC(0-t) µg * hr/mL | AUC(0-inf) µg * hr/mL | t½ hr |
| 1 | DECAB | 2 | 5.96 | 1.00 | 42.6 | 58.0 | 5.99 |
| 2 | BCADE | 5 | 7.45 | 2.00 | 50.0 | 61.4 | 4.47 |
| 3 | CDBEA | 4 | 7.39 | 2.00 | 46.3 | 56.7 | 4.62 |
| 4 | ABECD | 3 | 7.08 | 2.00 | 49.6 | — | — |
| 5 | CDBEA | 4 | 8.09 | 2.00 | 46.3 | 54.4 | 4.02 |
| 6 | DECAB | 2 | 7.62 | 1.00 | 43.8 | 57.1 | 5.59 |
| 7 | ABE___ | 3 | 8.09 | 2.00 | 48.9 | 58.2 | 4.07 |
| 8 | BCADE | 5 | 6.74 | 1.01 | 44.3 | 55.3 | 4.83 |
| Mean | | | 7.30 | 1.63 | 46.5 | 57.3 | 4.80 |
| SD | | | 0.711 | 0.516 | 2.80 | 2.26 | 0.744 |
| CV (%) | | | 9.74 | 31.7 | 6.03 | 3.94 | 15.5 |
| SEM | | | 0.251 | 0.182 | 0.991 | 0.854 | 0.281 |
| N | | | 8.00 | 8.00 | 8.00 | 7.00 | 7.00 |
| Median | | | 7.42 | 2.00 | 46.3 | 57.1 | 4.62 |
| Minimum | | | 5.96 | 1.00 | 42.6 | 54.4 | 4.02 |
| Maximum | | | 8.09 | 2.00 | 50.0 | 61.4 | 5.99 |
| Geom. Mean | | | 7.27 | — | 46.4 | 57.3 | — |

| | Parameters | | | | |
|---|---|---|---|---|---|
| Subject | Kel | | ln-Parameters | | |
| Number | 1/hr | AUCR | ln(Cmax) | ln[AUC(0-t)] | ln[AUC(0-inf)] |
| 1 | 0.116 | 0.735 | 1.79 | 3.75 | 4.06 |
| 2 | 0.155 | 0.815 | 2.01 | 3.91 | 4.12 |
| 3 | 0.150 | 0.816 | 2.00 | 3.83 | 4.04 |
| 4 | — | — | 1.96 | 3.90 | — |
| 5 | 0.172 | 0.850 | 2.09 | 3.83 | 4.00 |
| 6 | 0.124 | 0.767 | 2.03 | 3.78 | 4.04 |
| 7 | 0.170 | 0.841 | 2.09 | 3.89 | 4.06 |
| 8 | 0.144 | 0.802 | 1.91 | 3.79 | 4.01 |
| Mean | 0.147 | 0.804 | 1.98 | 3.84 | 4.05 |
| SD | 0.0216 | 0.0405 | 0.101 | 0.0604 | 0.0391 |

TABLE D$_{sub5}$-continued

Plasma Flucytosine Pharmacokinetic Parameters Following Administration
of 1 × 500 mg Flucytosine IR Capsule (Reference Formulation - Ancobon,
Valeant Pharmaceuticals) PO under Fasted Conditions (Treatment E)

| | | | | | |
|---|---|---|---|---|---|
| CV (%) | 14.6 | 5.04 | 5.11 | 1.57 | 0.966 |
| SEM | 0.00815 | 0.0153 | 0.0358 | 0.0213 | 0.0148 |
| N | 7.00 | 7.00 | 8.00 | 8.00 | 7.00 |
| Median | 0.150 | 0.815 | 2.00 | 3.83 | 4.04 |
| Minimum | 0.116 | 0.735 | 1.79 | 3.75 | 4.00 |
| Maximum | 0.172 | 0.850 | 2.09 | 3.91 | 4.12 |
| Geom. Mean | — | — | — | — | — |

— = Value missing or not reportable.

These data show that, whereas the AUC for Ancobon in fasted individuals (57.3 μg·h/ml) is approximately unchanged compared to fed individuals, with the Carbopol (54.3 μg·h/ml) and Kollidon (47.7 μg·h/ml) formulations, the $T_{max}$ is shifted from 1.63 h (Ancobon) to 5.62 h (Carbopol) and 7.86 h (Kollidon).

Example 26

Additional studies were performed in animals to assess single and multi-dose therapies. Three male beagle dogs were used for the study. On Day 1, the dogs received 500 mg of 5-fluorocytosine with formulation shown in Example 19, in the reference formulation, Ancobon® as a single oral dose after an overnight fast. On Day 5, the dogs received 500 mg 5-fluorocytosine in the extended release (5-FC-ER) tablet formulation (shown in Example 19) as a single oral dose after an overnight fast. On Days 1 and 5, fasting was continued for 4 hr after dosing. On Day 8, the dogs received a single oral dose of 500 mg 5-FC-ER, and from Day 9 through Day 12, the dogs received three daily doses of 500 mg 5-FC-ER with 7-hr intervals between the three doses. On Day 14, the dogs received 500 mg 5-fluorocytosine in the reference formulation, Ancobon®, as a single oral dose 30 minutes or more after being fed. All doses were administered with approximately 25 mL of water.

Blood samples, 2 mL, were collected from the jugular vein by direct venipuncture. Heparin was used as the anticoagulant. After centrifugation, the plasma was stored at −70±10° C. until analysis.

On Day 1, samples were collected pre-dose and at 0.25, 0.5, 0.75, 1, 2, 4, 8, 12 and 24 hr post-dose. On Day 5, samples were collected pre-dose and at 0.25, 0.5, 1, 2, 4, 8, 12, 24 and 48 hr post-dose. On Day 8, samples were collected pre-dose and at 0.5, 1, 2, 4, 8, 12 and 24 hr. On Days 9 through 12, samples were collected before each dose at 0, 7, 14, 24, 31, 38, 48, 55, 62, 72, 82, 86 hr and at 96 and 120 hr after the first dose on Day 9 (10 and 48 hr after the last dose on Day 12.

Determination of 5-Fluorocytosine. The concentrations of 5-fluorocytosine in the plasma samples were determined using a high pressure liquid chromatography (HPLC) method. The calibration range was from 1 to 100 μg/mL for a sample volume of 0.2 mL. The lower limit of quantitation was 1 μg/mL.

Noncompartmental pharmacokinetic parameters were calculated using WinNonlin 5.0.1. Excel 2003 was used to calculate the mean values and prepare the graphs. The maximum concentration, $C_{max}$ and time of maximum concentration, $T_{max}$ were determined as the maximum measured concentration and its associated time. The areas under the plasma concentration curve from 0 to 24 hr, $AUC_{0-24}$, and from 0 hr to the last measurable concentration ($AUC_{0-t}$), were calculated using linear trapezoidal estimation. All values reported as below the limit of quantitation, 1 μg/mL, were assumed to be zero for the calculations. Values for the half-life, $t_{1/2}$ were calculated using the last three to five non-zero values. Values for $AUC_{0-\infty}$ were estimated using an extrapolation from $AUC_{0-t}$ and the inverse of $t_{1/2}$. Results for $AUC_{0-\infty}$ and $t_{1/2}$ were considered reliable if the correlation coefficient for the fit to the data was 0.8.

The data from the multiple-dosing phase (Days 9 to 12) was compared with a projection using the mean values for the single dose on Day 8 of 500 mg of 5-FC ER after a meal. Using Excel, intermediate concentrations for a single dose were interpolated, and concentrations after 24 hr were determined by extrapolation using a half-life of 4.95 hr ($k_e$=0.140 hr$^{-1}$). The estimated single dose concentrations were offset by 7 hr and summed to reach the projected concentrations during multiple dosing.

Figure 2:
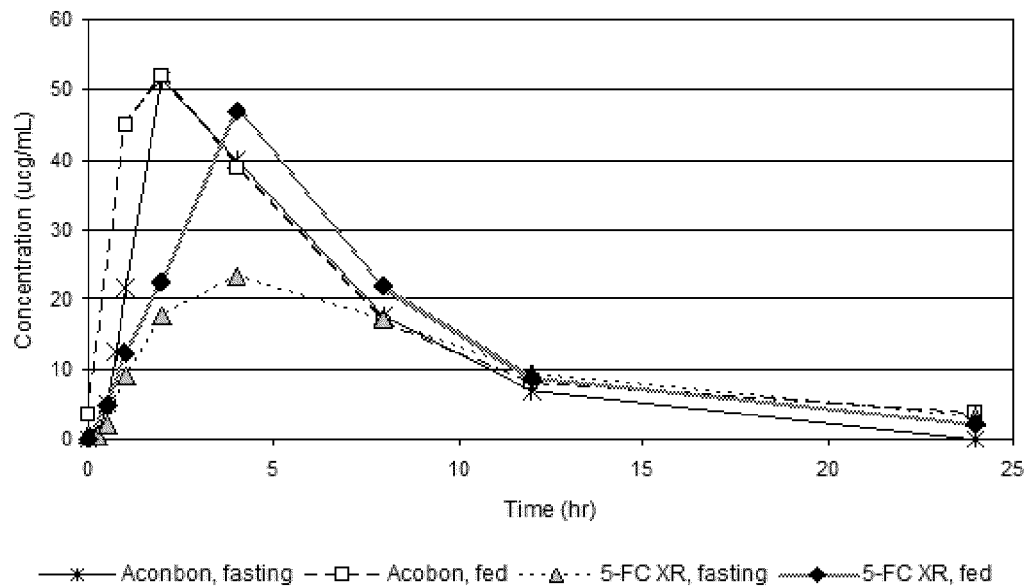
FIG. 2 shows the mean concentrations for male dogs receiving single doses of 500 mg 5-fluorocytosine (linear plot).
Figure 3:
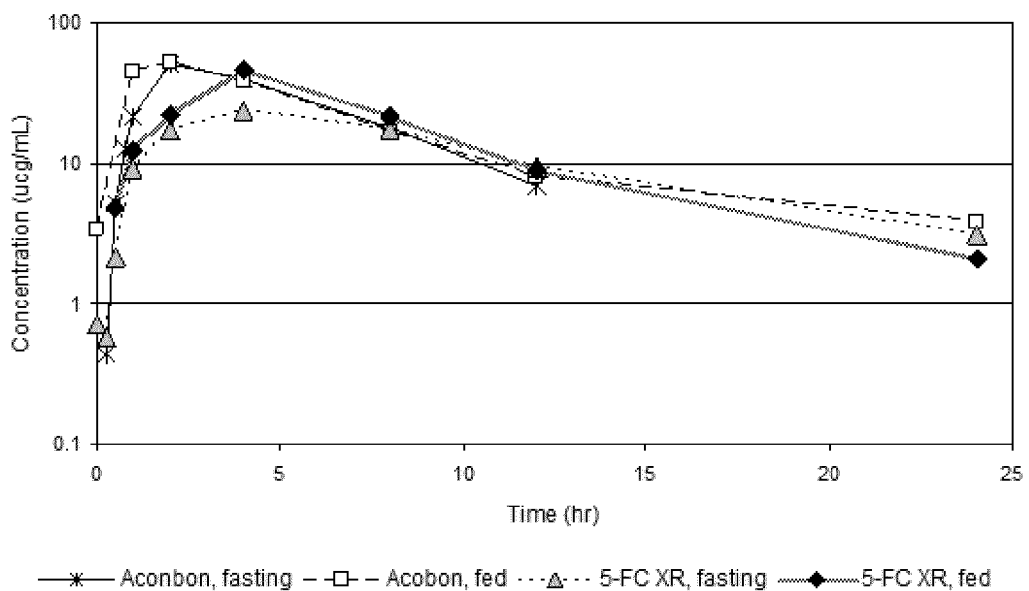
FIG. 3 shows mean concentrations for male dogs receiving single doses of 500 mg 5-fluorocytosine (semilog plot).
Figure 4:
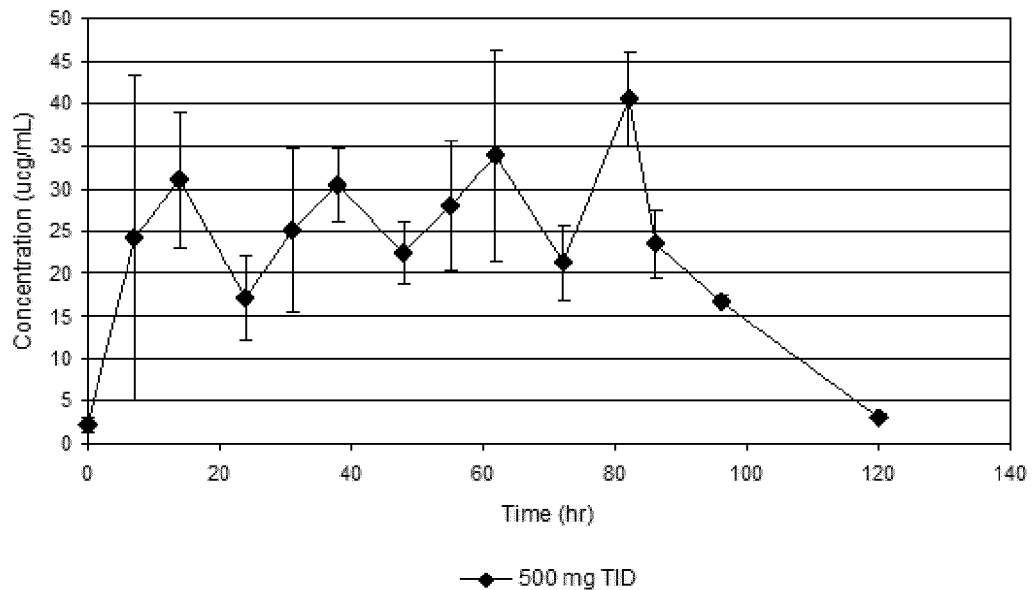
FIG. 4 shows mean concentrations for male dogs receiving 500 mg 5-FC XR TID (linear plot).

One dog treated with Ancobon® vomited soon after oral administration. No 5-FC XR treated dogs vomited. Plasma Levels of 5-Fluorocytosine. Tables E and F show the mean concentrations and associated standard deviations for 5-fluorocytosine after single doses and during multiple dosing, respectively. FIGS. 2 and 3 show linear and semilog plots of the mean concentrations for dogs receiving single doses of 5-fluorocytosine.

For Ancobon®, the plasma profiles of 5-fluorocytosine concentrations were similar after administration with and without food. However, for 5-FC ER, administration with food increased the peak plasma concentrations substantially. Compared to Ancobon®, the peak mean concentrations of 5-fluorocytosine occurred later for 5-FC ER, whether administered with food or in the fasting state. With food, the mean plasma concentrations of 5-FC ER were similar to the mean plasma concentrations of Ancobon®; however, in the fasting state, the mean plasma concentrations tended to be lower with 5-FC ER than with Ancobon up to the 8-hr sampling time when the mean concentrations were similar for both formulations.

Pharmacokinetic Parameters for 5-Fluorocytosine. Table G shows the mean values and associated standard deviations for the pharmacokinetic parameters for 5-fluorocytosine after single oral doses.

The presence of food had minimal or no effect on the $C_{max}$ values for Ancobon®. The mean $C_{max}$ with food was only 5% greater than the mean $C_{max}$ without food. However, the mean $C_{max}$ for 5-FC ER was approximately twice as high as the mean $C_{max}$ without food.

The effect of food on the AUC values was similar for both formulations. With food, the mean $AUC_{0-t}$, $AUC_{0-24}$ and $AUC_{0-\infty}$ for Ancobon were 32%, 16% and 33% higher, respectively, than the corresponding values without food. For 5-FC ER, the mean $AUC_{0-t}$, $AUC_{0-24}$ and $AUC_{0-\infty}$ values with food were 34%, 34% and 25% higher, respectively, than the corresponding values without food.

With food, mean $T_{max}$ was 25% shorter for Anconbon® and 20% longer for 5-FC ER compared to the corresponding fasted values. Given the small number of animals and the spacing between sampling times (particularly after 2 hr), the results with and without food can be considered to be similar with no apparent effect of food on $T_{max}$.

With food compared to fasting, the mean $t_{1/2}$ value was longer for Ancobon and shorter for 5-FC ER. Given the small number of animals and the spacing between sampling times, these apparent changes in $t_{1/2}$ may or may not reflect real changes due to food. For Ancobon®, with very little change in $C_{max}$ with food, the increase in apparent $t_{1/2}$ is probably responsible for the increases in the AUC values. For 5-FC ER, the apparent decrease in $t_{1/2}$ with food offset some of the contribution to AUC by the large increase in $C_{max}$ with food.

These results indicate that food increased the maximum exposure, as measured by $C_{max}$, to 5-fluorocytosine after administration of 5-FC ER, but had little or no effect on $C_{max}$ after administration of Ancobon®. The total exposure, as measured by $AUC_{0-t}$, increased with food by approximately $\frac{1}{3}^{rd}$ for both Ancobon® and 5-FC ER.

Table H shows the ratios that compare 5-FC ER to Ancobon for $C_{max}$, $T_{max}$, $AUC_{0-t}$ and $AUC_{0-\infty}$. These are measures of relative bioavailability of the formulations. For the overall extent of bioavailability, as measured by $AUC_{0-t}$, 5-FC ER was 88% of Ancobon® when both formulations were administered in the fasted state, and 5-FC ER was 85% of Ancobon when both formulations were administered in the fed state. $C_{max}$ and $T_{max}$ are measures of the rate of release and absorption of 5-fluorocytosine from the formulations. In the fasted state, $C_{max}$ for 5-FC ER was 48% of $C_{max}$ for Ancobon®, and $T_{max}$ occurred at 2 or 4 hr for 5-FC ER and at 2 hr for Ancobon. In the fed state, $C_{max}$ for 5-FC ER was 88% of $C_{max}$ for Ancobon®, and $T_{max}$ occurred at 4 hr for 5-FC ER and at 1 or 2 hr for Ancobon®. These results indicated an extended release and absorption of 5-fluorocytosine from 5-FC ER compared to Ancobon®, particularly in the fed state.

Figure 5:
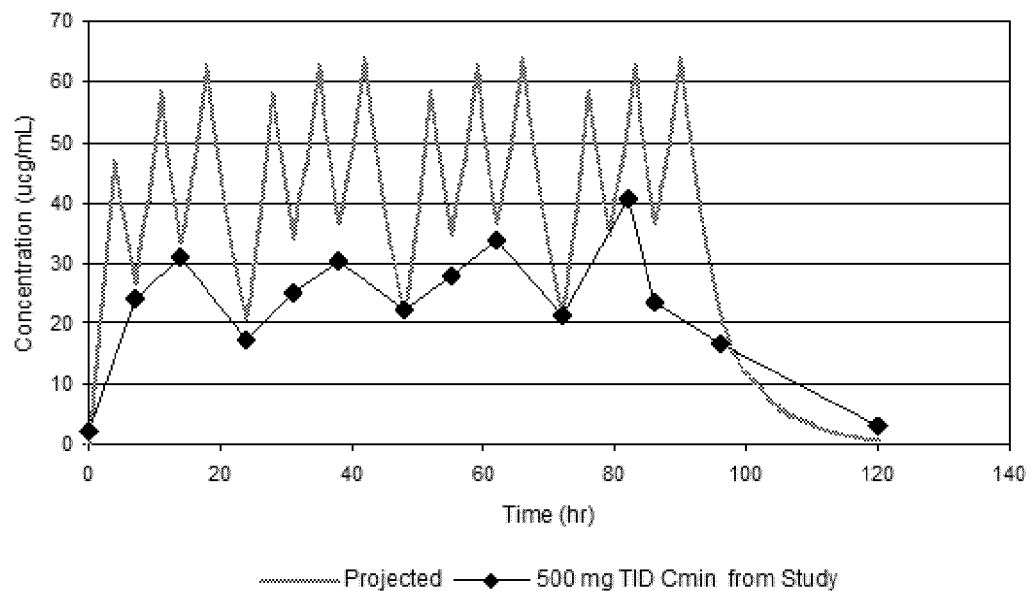
FIG. 5 shows projected and actual concentrations for dogs receiving 500 mg 5-FC TID with food (linear plot).

The mean concentrations for 5-fluorocytosine on Day 5 (5-FC ER administered after food) were used to project the concentrations that might be expected with the TID dosing schedule used on Days 9 through 12. The results of the projection are shown in FIG. 5. There was an excellent correlation between the observed concentrations and the projected concentrations for the samples taken before the first doses administered on Days 9 through 12. The correlations were also very good for the intra-day minimum pre-dose values on Day 9 and the post dosing samples taken on Days 13 and 14 (96 and 120 hr). Intraday on Days 10, 11 and 12, the measured concentrations tended to be lower than the projected concentrations. Since food affects the release of 5-fluorocytosine from 5-FC ER, it is possible that variations in the quantity and timing of food relative to dosing may be responsible for the lower measured concentrations. Overall, the projected concentrations were in fairly good agreement with the measured concentrations during TID dosing.

Food increased the maximum exposure, as measured by $C_{max}$, to 5-fluorocytosine after administration of 5-FC ER, but had little or no effect on $C_{max}$ after administration of Ancobon. The total exposure, as measured by $AUC_{0-t}$, increased with food by approximately $\frac{1}{3}^{rd}$ for both Ancobon and 5-FC ER. For relative bioavailability, as measured by $AUC_{0-t}$, 5-FC ER was 88% of Ancobon when both formulations were administered in the fasted state, and 5-FC ER was 85% of Ancobon when both formulations were administered in the fed state. There was an extended release and absorption of 5-fluorocytosine from 5-FC ER compared to Ancobon, particularly in the fed state. Overall, the concentrations projected from a single dose were in fairly good agreement with the measured concentrations during TID dosing.

TABLE E

Mean Plasma Concentrations of 5-Fluorocytosine for Male Dogs After Single Doses of 500 mg

| | Plasma Concentrations (µg/mL) | | | |
|---|---|---|---|---|
| Time (hr) | Day 1: Ancobon Fasting n = 3 Mean ± SD | Day 14: Ancobon Fed n = 2 Mean ± SD | Day 5: 5-FC XR Fasting n = 3 Mean ± SD | Day 8: 5-FC XR Fed n = 3 Mean ± SD |
| 0 | 0 | 3.37 | 0.703 ± 1.218 | 0 |
| 0.25 | 0.430 ± 0.745 | ns | 0.580 ± 1.005 | 4.81 ± 4.17 |
| 0.5 | 5.20 ± 5.30 | ns | 2.13 ± 2.21 | ns |
| 0.75 | 12.7 ± 6.6 | ns | ns | ns |
| 1 | 21.7 ± 9.1 | 45.1 | 9.06 ± 5.43 | 12.4 ± 8.8 |
| 2 | 51.4 ± 5.2 | 52.0 | 17.6 ± 1.3 | 22.5 ± 14.5 |
| 4 | 39.8 ± 6.3 | 38.9 | 23.4 ± 7.6 | 46.8 ± 3.2 |
| 8 | 17.8 ± 6.3 | 16.7 | 17.1 ± 6.0 | 21.9 ± 3.5 |
| 12 | 6.91 ± 3.51 | 8.05 | 9.36 ± 4.39 | 8.81 ± 3.10 |
| 24 | 0 | 3.81 | 3.13 ± 0.15 | 2.11 ± 0.87 | ns = no sample collection.
Standard deviations were not calculated when all values were 0 or when n < 3.

TABLE F

Mean Plasma Concentrations of 5-Flurocytosine for Male Dogs Receiving 500 mg 5-FC XR TID

| Day | Time (hr) | Relationship to Dose | Concentration (µg/mL) Mean ± SD |
|---|---|---|---|
| 9 | 0 | Pre-dose | 2.11 ± 0.87 |
| 9 | 7 | Pre-dose | 24.2 ± 19.1 |
| 9 | 14 | Pre-dose | 31.0 ± 7.9 |
| 10 | 24 | Pre-dose | 17.3 ± 5.1 |
| 10 | 31 | Pre-dose | 25.2 ± 9.7 |
| 10 | 38 | Pre-dose | 30.5 ± 4.2 |
| 11 | 48 | Pre-dose | 22.4 ± 3.8 |
| 11 | 55 | Pre-dose | 27.9 ± 7.7 |
| 11 | 62 | Pre-dose | 33.9 ± 12.3 |
| 12 | 72 | Pre-dose | 21.3 ± 4.5 |
| 12 | 82 | 3 hr post-dose | 40.5 ± 5.5 |
| 12 | 86 | Pre-dose | 23.5 ± 4.1 |
| 13 | 96 | 10 hr Post-dose | 16.8 ± 0.6 |
| 14 | 120 | 34 hr Post-dose | 3.17 ± 0.35 | n = 3 in all cases.

TABLE G

Mean Pharmacokinetic Parameters for 5-Fluorocytosine for Male Dogs

| Formulation | Day | Food | $C_{max}$ (μg/mL) Mean ± SD | $T_{max}$ (hr) Mean ± SD | $AUC_{0-t}$ (μg · hr/mL) Mean ± SD | $AUC_{0-24}$ (μg · hr/mL) Mean ± SD | $AUC_{0-\infty}$ (μg · hr/mL) Mean ± SD | $t_{1/2}$ (hr) Mean ± SD |
|---|---|---|---|---|---|---|---|---|
| Ancobon | 1 | Fasted | 51.4 ± 4.3 | 2.0 ± 0.0 | 300 ± 31 | 341 ± 48 | 333 ± 48 | 3.10 ± 0.56 |
| Ancobon | 14 | Fed | 54.2$^a$ | 1.5$^a$ | 395$^a$ | 395$^a$ | 441$^a$ | 8.31$^a$ |
| % Difference | | | 5% | −25% | 32% | 16% | 33% | 168% |
| 5-FC XR | 5 | Fasted | 24.0 ± 5.6 | 3.3 ± 0.9 | 267 ± 66 | 267 ± 66 | 298 ± 59 | 7.00 ± 1.30 |
| 5-FC XR | 8 | Fed | 46.8 ± 2.6 | 4.0 ± 0.0 | 358 ± 34 | 358 ± 34 | 373 ± 39 | 4.87 ± 0.49 |
| % Difference | | | 95% | 20% | 34% | 34% | 25% | −30% | n = 3, except when noted.
$^a$n = 2; Standard deviations were not calculated when n < 3.

TABLE H

Ratios of Parameter for 5-FC XR Compared to Parameters for Ancobon

| | | Ratio of 5-FC XR/Ancobon | | | |
|---|---|---|---|---|---|
| Food | Dog No. | $C_{max}$ | $T_{max}$ | $AUC_{0-t}$ | $AUC_{0-\infty}$ |
| Fasted | 4872380 | 0.326 | 1.00 | 0.705 | 0.822 |
| | 5717787 | 0.427 | 2.00 | 0.890 | 0.892 |
| | 5730597 | 0.678 | 2.00 | 1.03 | 0.951 |
| | Mean | 0.477 | 1.67 | 0.876 | 0.888 |
| | SD | 0.181 | 0.58 | 0.165 | 0.065 |
| Fed | 4872380 | 1.03 | 2.00 | 0.850 | 0.818 |
| | 5717787 | 0.726 | 4.00 | 0.845 | 0.759 |
| | Mean | 0.878 | 3.00 | 0.848 | 0.789 |

Standard deviations were not calculated when n < 3.

Example 27

Glioblastoma Multiforme Treatment.

A recombinant retroviral vector comprising an IRES cassette linked to a cytosine deaminase coding sequence can be injected transcranially into the subject's tumor. The surgeon will use a stereotactic (either frame-based or neuronavigational) technique to identify an area of tumor corresponding to a region of enhancement on gadolinium-enhanced MRI scan. A burr hole will be created and a Nashold needle will be inserted into the tumor. A frozen section will be obtained to confirm that the needle is seated in tumor and then 1 ml of the retroviral vector will be injected down the bore of the needle. After 3 minutes the needle will be slowly removed and the entry site closed. Because the vector is a replication competent virus, there is limited need to make multiple injections into the brain. Each patient will receive only a single injection, although different tumor and cancer locations may be injected either temporally or spatially.

5-FC is generally well tolerated in patients with normal renal function. The standard dose of 5-FC used to treat fungal infections is 50-150 mg/kg/day administered in 4 divided doses. In animal studies, 5-FC was dosed at 500 mg/kg intraperitoneally once daily. This dose is equivalent on a per meter-squared basis to approximately 50 mg/kg in humans. However, because many studies have documented the variability of serum flucytosine concentrations following oral dosing, the mid-range dose of 100 mg/kg/day will be chosen as the starting dose or ramp dose, and determination of the peak plasma concentration will be used to optimize 5-FC dosing. Following an initial dosing to obtain the desired plasma concentration of 5-FC an extended release formulation can be administered (either monolithic modified-release dosage forms (MMR) polymer encapsulated, SiO2 encapsulated or alginate encapsulated). The extended release formula can comprise any of the foregoing formulations. The purpose of the extended release formulation is to assist in patient compliance and adverse side effects typically resulting from large dosing regimen with standard Ancobon®.

Doses can be adjusted based on monitoring of peak serum flucytosine levels either during or prior to long term drug maintenance.

A dose will contain ~$10^6$ TU/ml (i.e., transforming unit (TU) refers to the number of retroviral genomes present in a transfected cell in a standard vector titering test). Following the first dose of 5-FC, the peak 5-FC plasma concentration will be determined and the dose of 5-FC adjusted to maintain the peak concentration in the range of 50-80 μg/ml. If tolerated the extended release dosing is repeated at an administration of 4 or less times per day for 7 days. Tumor response is assessed using the Macdonald criteria. A standard dose-escalation algorithm will be followed. Three patients will be evaluated at each dose level ($10^6$, $10^7$, $10^8$, TU/ml). There will be no intra-patient dose escalation.

5-FC will be administered at between about 1-250 mg/kg/day (e.g., about 1-200 mg/kg, about 1-175 mg/kg, about 1-150 mg/kg, or about 1-100 mg/kg per day) in 1 or more divided doses. Peak serum concentration can be measured by drawing blood 1-2 hours following a dose of flucytosine. The specimen will be split and half run at the site to provide immediate information regarding the dose, and half sent to the central lab for later correlation. The peak flucytosine concentration should be between about 50 and 80 μg/mL.

A number of embodiments of the invention have been described. Nevertheless, it will be understood that various modifications may be made without departing from the spirit and scope of the invention. Accordingly, other embodiments are within the scope of the following claims.

What is claimed is:

1. An oral pharmaceutical composition comprising 5-fluorocytosine (FC), wherein the pharmaceutical composition is a monolithic solid tablet form comprising at least one hydrophilic matrix forming polymer of about 5 weight percent to about 40 weight percent, at least one diluent of about 10 weight percent to about 40 weight percent and at least one binder of about 0.5 weight percent to about 30 weight percent and wherein the pharmaceutical composition is restricted to the upper gastrointestinal tract and releases 5-FC into the upper gastrointestinal tract of a subject over a sustained period of time, wherein the composition has an in vitro 5-FC dissolution rate of less than 33% at 0.5 hours in pH 1.2.

2. The pharmaceutical composition of claim 1, further comprising at least two hydrophilic matrix forming polymer.

3. The pharmaceutical composition of claim 1, wherein the hydrophilic matrix forming polymer is one or more of carbomer, polyvinyl acetate and povidone based polymer, hydroxypropyl cellulose (HPC), hydroxymethyl cellulose (HPMC), and polyethylene oxide (PolyOx).

4. The pharmaceutical composition of claim 3, wherein the hydrophilic matrix forming polymers make up about 10 weight percent to about 40 weight percent of the composition.

5. The pharmaceutical composition of claim 1, wherein 5-FC is present in an amount of about 100 mg to about 2000 mg.

6. The pharmaceutical composition of claim 1, wherein the composition exhibits a 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

7. The pharmaceutical composition of claim 1, wherein after a single dose oral administration to a fed subject the composition exhibits: (i) a $t_{median}$ of about 3 hrs or greater; (ii) a $t_{max}$ of about 3 hrs or greater; and (iii) a $t_{1/2}$ of between about 3-8 hrs.

8. The pharmaceutical composition of claim 1, wherein 5-FC is present in the pharmaceutical composition in an amount of about 500 mg, after single oral administration of the 500 mg pharmaceutical composition to a fed subject, the composition exhibits one or more of the following: (i) a 5-FC $C_{max}$ of between about 2.0 µg/ml and about 10.0 µg/ml; (ii) a $t_{max}$ of about 3 hrs or greater; (iii) an $AUC_\infty$ of about 20-80 µg*hr/ml; and (iv) a $t_{1/2}$ of between about 3-8 hrs.

9. The pharmaceutical composition of claim 5, wherein the AUC in a fed human subject after a single administration of a 2 gram composition provides an AUC of 15-40 µg·hr/mL over a 24 hour period.

10. The pharmaceutical composition of claim 5, wherein the AUC in a fed human subject administered 2 gram 5-FC provides an AUC of 100-150 µg·hr/mL over a 24 hour period.

11. The pharmaceutical composition of claim 5, wherein following administration of 2 grams 5-FC to a fed human subject the 5-FC concentration in the serum during a 24 hour period is above 10 µg/ml for about 5-15 hours.

12. The pharmaceutical composition of claim 5, wherein following daily administration for about 7 days or about 5 half-lives or more with 1-250 mg/Kg/day in divided doses to a fed human subject the mean serum concentration of 5-FC during a 24 hour period is about 1-200 µg/ml.

13. The pharmaceutical composition of claim 12, wherein following a repeated dose for 6 weeks with 1-250 mg/Kg/day in divided doses to a fed human subject the mean serum concentration of 5-FC during a 24 hour period is about 1-200 µg/ml.

14. The pharmaceutical composition of claim 12, wherein following daily administration for 7 days or about 5 half-lives or more with 1-250 mg/Kg/day in divided doses to a fed human subject the mean serum concentration of 5-FC during a 24 hour period is about 30-80 µg/ml.

15. The pharmaceutical composition of claim 8, wherein the composition is administered 1-4 times per day.

16. A pharmaceutical composition according to claim 1, where the total AUC in a fed human is about 75-125% of a current immediate release formulation of 5-FC.

17. A method of treating a fungal infection by administering a pharmaceutical composition of claim 1.

18. A method of treating cancer in a mammal by administering a pharmaceutical composition of claim 1 in conjunction with a polypeptide comprising cytosine deaminase activity to treat cancer in a mammal.

19. A method of treating cancer in a mammal by administering a pharmaceutical composition of claim 1 in conjunction with a polynucleotide encoding a cytosine deaminase to treat cancer in a mammal.

20. A method of treating cancer in a mammal having previously received cytosine deaminase gene therapy comprising administering to the mammal a pharmaceutically effective amount of a composition of claim 1.

21. A method of claim 19, wherein the polynucleotide encoding a cytosine deaminase is delivered with a viral vector.

22. A method of claim 19, wherein the polynucleotide encoding a cytosine deaminase is delivered with a non-viral vector.

23. The method of claim 21, wherein the viral vector is retroviral vector or an adenoviral vector.

24. The method of claim 23, wherein the retroviral vector is a non-replication competent retroviral vector, a replication competent retroviral vector or a recombinant replication retroviral vector.

25. The method of claim 24, wherein the replication competent retroviral vector comprises an oncoretroviral vector.

26. The method of claim 25, wherein the replication competent retroviral vector comprises an internal ribosomal entry site (IRES) 5' to the polynucleotide encoding a cytosine deaminase.

27. The method of claim 26, wherein the polynucleotide encoding a cytosine deaminase is 3' to a ENV polynucleotide.

28. The method of claim 17, wherein the fungal infection is an infection by a fungus selected from the group consisting of *Candida* spp., *Cryptococcus* spp., *Sporothrix* spp., *Aspergillus* spp., *Cladosporium* spp., *Exophila* spp. and *Phialophora* spp.

29. The method of claim 17, further comprising administration of a fungus-treating effective amount of amphotericin B, fluconazole, leukovorin or itraconazole.

30. The method of claim 17, wherein the fungal disease is a foot fungal disease.

31. A method of treating a cancer comprising administering to a subject in need thereof a sufficient amount of an expression vector comprising a cytosine deaminase which is capable of converting 5-fluorocytosine to 5-fluorouracil in cells of the cancer and a cancer-treating effective amount of a composition of claim 1.

32. The method of claim 31, wherein the cancer comprises a solid tumor.

33. The method of claim 31, wherein the composition is administered one, two or three times per day.

34. The method of claim 31, wherein the expression vector is a retroviral vector or an adenoviral vector.

35. The method of claim 34, wherein the retroviral vector is a replication competent retroviral vector, a replication defective retroviral vector or a recombinant replication competent retroviral vector.

36. The method of claim 31, wherein the method further comprises administering leukovorin.

37. A method of treating a subject with a cancer, comprising:
   identifying a tumor size;
   determining the number of therapeutic units of a replication competent retroviral vector comprising a cassette having an IRES linked to a polynucleotide encoding a cytosine deaminase;
   calculating a dose of a 5-FC formulation based upon the tumor size and therapeutic units;
   administering the replication competent retroviral vector to the subject;
   administering the dose of a 5-FC formulation.

38. The method of claim 37, wherein the dose comprises about 1-250 mg/kg administered 1 to 4 times per day.

39. The method of claim 38, further comprising determining a subject's renal function.

40. The method of claim 38, further comprising determining a subject's creatinine clearance.

41. An oral extended release formulation comprising 5-Fluorocytosine (5-FC), wherein said formulation is a monolithic solid tablet form comprising at least one hydrophilic matrix forming polymer of about 5 weight percent to about 40 weight percent, at least one diluent of about 10 weight percent to about 40 weight percent, and at least one binder of about 0.5 weight percent to about 30 weight percent and wherein the formulation provides enhanced bioavailability with food and wherein upon administration the ratio of the AUC in the fed state over the AUC in the fasted state has a value selected from the group consisting of: (i) about 1.5 to about 3.0; (ii) about 1.8 to about 2.5; and (iii) about 1.9 to about 2.3.

42. The oral extended release formulation of claim 41, wherein the hydrophilic matrix forming polymer is one or more of carbomer, polyvinyl acetate and povidone based polymer, hydroxypropyl cellulose (HPC), hydroxymethyl cellulose (HPMC), and polyethylene oxide (PolyOx).

43. The oral extended release formulation of claim 42, wherein the hydrophilic matrix forming polymers make up about 10 weight percent to about 40 weight percent of the composition.

44. The oral extended release formulation of claim 43, wherein 5-FC is present in an amount of about 100 mg to about 2000 mg.

45. The oral extended release formulation of claim 41, wherein the composition exhibits 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

46. An oral extended release formulation comprising 5-Fluorocystosine in a monolithic solid tablet form comprising at least one hydrophilic matrix forming polymer of about 5 weight percent to about 40 weight percent, at least one diluent of about 10 weight percent to about 40 weight percent, and at least one binder of about 0.5 weight percent to about 30 weight percent and wherein upon administration the ratio of $C_{max}$ fed/$C_{max}$ fasted has a value selected from the group consisting of (i) about 1.5 to about 3.0 and (ii) about 1.8 to about 2.4.

47. The oral extended release formulation of claim 46, wherein the hydrophilic matrix forming polymer is one or more of carbomer, polyvinyl acetate and povidone based polymer, hydroxypropyl cellulose (HPC), hydroxymethyl cellulose (HPMC), and polyethylene oxide (PolyOx).

48. The oral extended release formulation of claim 47, wherein the hydrophilic matrix forming polymers make up about 10 weight percent to about 40 weight percent of the composition.

49. The oral extended release formulation of claim 48, wherein 5-FC is present in an amount of about 100 mg to about 2000 mg.

50. The oral extended release formulation of claim 46, wherein the composition exhibits 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

51. An oral extended release formulation comprising 5-Fluorocytosine in a monolithic solid tablet form comprising at least one hydrophilic matrix forming polymer of about 5 weight percent to about 40 weight percent, at least one diluent of about 10 weight percent to about 40 weight percent, and at least one binder of about 0.5 weight percent to about 30 weight percent and wherein said formulation provides enhanced bioavailability with food and wherein upon administration the $AUC_{0-inf}$ in the fed state is greater than about 70% of the AUC in the fasted state of flucytosine immediate release.

52. The formulation of claim 51, wherein said AUC in the fed state is less than about 125% of the AUC in the fasted state of flucytosine immediate release.

53. The formulation of claim 51, wherein said AUC in the fed state is about 80-100% of the AUC in the fasted state for flucytosine immediate release.

54. The formulation of claim 51, wherein said AUC in the fed state is about 83-95% of the AUC in the fasted state for flucytosine immediate release.

55. The oral extended release formulation of claim 51, wherein the hydrophilic matrix forming polymer is one or more of carbomer, polyvinyl acetate and povidone based polymer, hydroxypropyl cellulose (HPC), hydroxymethyl cellulose (HPMC), and polyethylene oxide (PolyOx).

56. The oral extended release formulation of claim 55, wherein the hydrophilic matrix forming polymers make up about 10 weight percent to about 40 weight percent of the composition.

57. The oral extended release formulation of claim 56, wherein 5-FC is present in an amount of about 100 mg to about 2000 mg.

58. The oral extended release formulation of claim 51, wherein the composition exhibits 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

59. An oral extended release formulation comprising 5-Fluorocytosine in a monolithic solid tablet form comprising at least one hydrophilic matrix forming polymer of about 5 weight percent to about 40 weight percent, at least one diluent of about 10 weight percent to about 40 weight percent, and at least one binder of about 0.5 weight percent to about 30 weight percent and wherein upon administration the $C_{max}$ in the fed state is less than about 90% of the $C_{max}$ in the fasted state of flucytosine immediate release.

60. The formulation of claim 59, wherein said $C_{max}$ in the fed state is greater than about 30% of the $C_{max}$ in the fasted state of flucytosine immediate release.

61. The formulation of claim 59, wherein said $C_{max}$ in the fed state is about 50-85% of the $C_{max}$ in the fasted state for flucytosine immediate release.

62. The oral extended release formulation of claim 59, wherein the hydrophilic matrix forming polymer is one or more of carbomer, polyvinyl acetate and povidone based polymer, hydroxypropyl cellulose (HPC), hydroxymethyl cellulose (HPMC), and polyethylene oxide (PolyOx).

63. The oral extended release formulation of claim 62, wherein the hydrophilic matrix forming polymers make up about 10 weight percent to about 40 weight percent of the composition.

64. The oral extended release formulation of claim 59, wherein 5-FC is present in an amount of about 100 mg to about 2000 mg.

65. The oral extended release formulation of claim 59, wherein the composition exhibits 5-FC in vitro dissolution rate of greater than about 80% within about 4 to about 12 hours as measured by the USP Type II dissolution apparatus (paddle method) at 75 rpm in 900 ml water at 37° C. using 5-FC USP method with UV detection at about 275-285 nm.

66. An oral pharmaceutical monolithic tablet comprising 5-fluorocytosine (5-FC) and:
 (i) about 5% to about 15% of a binding agent;
 (ii) about 10% to about 30% of a diluent;
 (iii) about 10% to about 20% of at least one hydrophilic polymer; and
 (iv) about 1% to about 3% of a coating, wherein the composition has an in vitro 5-FC dissolution rate of less than 33% at 0.5 hours in pH 1.2.

67. The oral pharmaceutical composition of claim 66, wherein the 5-FC comprises about 500 mg/tablet.

68. The oral pharmaceutical composition of claim 66 comprising
 about 500 mg of 5-fluorocytosine;
 about 60 mg of hydroxypropyl cellulose;
 about 100 mg of dicalcium phosphate;
 about 110 mg of carbomer; and
 about 180 mg of microcrystalline cellulose.

* * * * *